United States Patent
Bell

(10) Patent No.: US 12,065,688 B2
(45) Date of Patent: *Aug. 20, 2024

(54) COMPOSITIONS AND METHODS FOR CELLULAR PROCESSING

(71) Applicant: 10X GENOMICS, INC., Pleasanton, CA (US)

(72) Inventor: Jason Bell, Palo Alto, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 624 days.

This patent is subject to a terminal disclaimer.

(21) Appl. No.: 16/434,095

(22) Filed: Jun. 6, 2019

(65) Prior Publication Data

US 2020/0056223 A1 Feb. 20, 2020

Related U.S. Application Data

(60) Provisional application No. 62/845,164, filed on May 8, 2019, provisional application No. 62/720,065, filed on Aug. 20, 2018.

(51) Int. Cl.
C12Q 1/6806 (2018.01)
(52) U.S. Cl.
CPC .... *C12Q 1/6806* (2013.01); *C12Y 301/31001* (2013.01)
(58) Field of Classification Search
None
See application file for complete search history.

(56) References Cited

U.S. PATENT DOCUMENTS

| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |

(Continued)

FOREIGN PATENT DOCUMENTS

| EP | 1019496 B1 | 9/2004 |
| EP | 1841879 A2 | 10/2007 |

(Continued)

OTHER PUBLICATIONS

Rotem et al., Single-cell ChIP-seq reveals cell subpopulations defined by chromatin state. Nat Biotechnol. Nov. 2015;33(11):1165-72. doi: 10.1038/nbt.3383. Epub Oct. 12, 2015. PMID: 26458175; PMCID: PMC4636926; cited as Non-Patent Literature Document #002, on IDS filed Jul. 25, 2019 (Year: 2015).*

(Continued)

*Primary Examiner* — Aaron A Priest
*Assistant Examiner* — Tian Nmn Yu
(74) *Attorney, Agent, or Firm* — Wilson Sonsini Goodrich & Rosati

(57) ABSTRACT

Provided herein are compositions and methods for cellular analysis. Nucleic acid from single cells may be processed in one or more partitions. A partition may comprise a cell bead and one or more enzymes for nucleic acid processing. A partition may comprise a functionalized polymer. In some cases, single cells may be subjected to epigenetic analysis, thereby generating an epigenetic profile for each cell from a plurality of cells.

19 Claims, 23 Drawing Sheets

(56) References Cited

U.S. PATENT DOCUMENTS

| | | |
|---|---|---|
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,005,935 B2 | 4/2015 | Belyaev |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,676,779 B2 * | 6/2020 | Chang ............... G01N 33/532 |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,459,607 B1 | 10/2022 | Terry et al. |
| 11,467,153 B2 | 10/2022 | Belhocine et al. |
| 11,655,499 B1 | 5/2023 | Pfeiffer |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | Mccloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |

(56) References Cited

U.S. PATENT DOCUMENTS

| | | |
|---|---|---|
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0066385 A1 | 3/2015 | Schnall-Levin et al. |
| 2015/0220532 A1 | 8/2015 | Wong |
| 2015/0267191 A1 | 9/2015 | Steelman et al. |
| 2015/0292988 A1 | 10/2015 | Bharadwaj et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0208323 A1 | 7/2016 | Bernstein et al. |
| 2016/0232291 A1 | 8/2016 | Sofia et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0071695 A1 | 3/2018 | Weitz et al. |
| 2018/0080021 A1 | 3/2018 | Reuter et al. |
| 2018/0080075 A1 | 3/2018 | Brenner et al. |
| 2018/0105808 A1 | 4/2018 | Mikkelsen et al. |
| 2018/0216162 A1 | 8/2018 | Belhocine et al. |
| 2018/0237951 A1 | 8/2018 | Bock et al. |
| 2018/0273933 A1 | 9/2018 | Gunderson et al. |
| 2018/0305685 A1 | 10/2018 | Li et al. |
| 2018/0312822 A1 | 11/2018 | Lee et al. |
| 2018/0312873 A1 | 11/2018 | Zheng |
| 2018/0334670 A1 | 11/2018 | Bharadwaj et al. |
| 2018/0340169 A1 | 11/2018 | Belhocine et al. |
| 2018/0340939 A1 | 11/2018 | Gaublomme et al. |
| 2018/0371545 A1 | 12/2018 | Wong et al. |
| 2019/0002967 A1 | 1/2019 | Chen et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0100632 A1 | 4/2019 | Delaney et al. |
| 2019/0127731 A1 | 5/2019 | Mcdermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2021/0190770 A1 | 6/2021 | Delaney et al. |
| 2021/0270703 A1 | 9/2021 | Abousoud |
| 2022/0033893 A1 * | 2/2022 | Lan .............. C12N 15/1044 |
| 2024/0002914 A1 | 1/2024 | Pfeiffer |

FOREIGN PATENT DOCUMENTS

| | | | |
|---|---|---|---|
| EP | 1841879 A4 | 5/2009 | |
| EP | 1967592 B1 | 4/2010 | |
| EP | 2540389 A1 | 1/2013 | |
| EP | 2954065 A2 * | 12/2015 | ......... C12N 15/1065 |
| EP | 2635679 B1 | 4/2017 | |
| GB | 2097692 A | 11/1982 | |
| GB | 2097692 B | 5/1985 | |
| WO | WO-84/02000 | 5/1984 | |
| WO | WO-95/30782 | 11/1995 | |
| WO | WO-99/52708 | 10/1999 | |
| WO | WO-2000008212 A1 | 2/2000 | |
| WO | WO-2001002850 A1 | 1/2001 | |
| WO | WO-0114589 A2 | 3/2001 | |
| WO | WO-0189787 A2 | 11/2001 | |
| WO | WO-0190418 A1 | 11/2001 | |
| WO | WO-2001089787 A9 | 11/2001 | |
| WO | WO-2004002627 A2 | 1/2004 | |
| WO | WO-2004065617 A2 | 8/2004 | |
| WO | WO-2004069849 A2 | 8/2004 | |
| WO | WO-2004091763 A2 | 10/2004 | |
| WO | WO-2004069849 A3 | 3/2005 | |
| WO | WO-2005021151 A1 | 3/2005 | |
| WO | WO-2005049787 A2 | 6/2005 | |
| WO | WO-2005082098 A2 | 9/2005 | |
| WO | WO-2005082098 A3 | 12/2005 | |
| WO | WO-2006040551 A2 | 4/2006 | |
| WO | WO-2004065617 A3 | 6/2006 | |
| WO | WO-2006078841 A1 | 7/2006 | |
| WO | WO-2006096571 A2 | 9/2006 | |
| WO | WO-2007081385 A2 | 7/2007 | |
| WO | WO-2007081387 A1 | 7/2007 | |
| WO | WO-2007089541 A2 | 8/2007 | |
| WO | WO-2007133710 A2 | 11/2007 | |
| WO | WO-2007140015 A2 | 12/2007 | |
| WO | WO-2007147079 A2 | 12/2007 | |
| WO | WO-2008021123 A1 | 2/2008 | |
| WO | WO-2007147079 A3 | 3/2008 | |
| WO | WO-2008109176 A2 | 9/2008 | |
| WO | WO-2008121342 A2 | 10/2008 | |
| WO | WO-2008134153 A1 | 11/2008 | |
| WO | WO-2008150432 A1 | 12/2008 | |
| WO | WO-2009011808 A1 | 1/2009 | |
| WO | WO-2009015296 A1 | 1/2009 | |
| WO | WO-2009085215 A1 | 7/2009 | |
| WO | WO-2009152928 A2 | 12/2009 | |

(56) References Cited

FOREIGN PATENT DOCUMENTS

| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2010148039 A3 | 7/2011 |
| WO | WO-2012048341 A1 | 4/2012 |
| WO | WO-2012061832 A1 | 5/2012 |
| WO | WO-2012083225 A2 | 6/2012 |
| WO | WO-2012083225 A3 | 8/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2012116331 A3 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2012106546 A3 | 11/2013 |
| WO | WO-2014028378 A2 | 2/2014 |
| WO | WO-2012142531 A3 | 5/2014 |
| WO | WO-2012166425 A3 | 5/2014 |
| WO | WO-2014108810 A2 | 7/2014 |
| WO | WO-2014165559 A2 | 10/2014 |
| WO | WO-2014108810 A3 | 12/2014 |
| WO | WO-2015015199 A2 | 2/2015 |
| WO | WO-2015044428 A1 | 4/2015 |
| WO | WO-2015164212 A1 | 10/2015 |
| WO | WO-2012142611 A3 | 3/2016 |
| WO | WO-2016040476 A1 | 3/2016 |
| WO | WO-2016033251 A3 | 4/2016 |
| WO | WO-2016061517 A2 | 4/2016 |
| WO | WO-2016061517 A3 | 6/2016 |
| WO | WO-2016126871 A2 * | 8/2016 .......... B01F 13/0071 |
| WO | WO-2016168584 A1 | 10/2016 |
| WO | WO-2017015075 A1 | 1/2017 |
| WO | WO-2017034970 A1 | 3/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A2 | 11/2017 |
| WO | WO-2018031631 A1 | 2/2018 |
| WO | WO-2018039338 A1 | 3/2018 |
| WO | WO-2018039969 A1 | 3/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019071039 A1 | 4/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020142779 A1 | 7/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
PCT/US2020/017785 Application filed on Feb. 11, 2020 by Ziraldo, Solongo B. et al.
PCT/US2020/017789 Application filed on Feb. 11, 2020 by Belhocine, Zahara Kamila et al.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Adamson et al., "Production of arrays of chemically distinct nanolitre plugs via repeated splitting in microfluidic devices", Lab Chip 6(9): 1178-1186 (Sep. 2006).
Braeckmans et al., Scanning the Code. Modern Drug Discovery. 2003:28-32.
Buchman GW, et al. Selective RNA amplification: a novel method using dUMP-containing primers and uracil DNA glycosylase. PCR Methods Appl. Aug. 1993; 3(1):28-31.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Drmanac et al., Sequencing by hybridization (SBH): advantages, achievements, and opportunities. Adv Biochem Eng Biotechnol. 2002;77:75-101.
Esser-Kahn, et al. Triggered release from polymer capsules. Macromolecules. 2011; 44:5539-5553.

(56) References Cited

OTHER PUBLICATIONS

Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Madl, et al. "Bioorthogonal Strategies for Engineering Extracellular matrices", Madal, Chritopher, Adv. Funct. Master. Jan. 19, 2018, vol. 28, 1706046, pp. 1-21.
Orakdogen, N. "Novel responsive poly(N,N-dimethylaminoethyl methacrylate) gel beads: preparation, mechanical properties and pH-dependent swelling behavior" J Polym Res (2012) 19:9914.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Ramskold et al. (2012) "Full-length mRNA-Seq from single-cell levels of RNA and individual circulating tumor cells" Nature Biotechnology 30(8):777-782.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Smith, et al. Highly-multiplexed barcode sequencing: an efficient method for parallel analysis of pooled samples. Nucleic Acids Research, 38(13): e142 (2010).
Thaxton, C.S. et al. "A Bio-Bar-Code Assay Based Upon Dithiothreitol Oligonucleotide Release" Anal Chem (2005) 77:8174-8178.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Zhang, et al. One-step fabrication of supramolecular microcapsules from microfluidic droplets. Science. Feb. 10, 2012;335(6069):690-4. doi: 10.1126/science.1215416.
Kelsey, et al. Single-cell epigenomics: Recording the past and predicting the future. Science. Oct. 6, 2017;358(6359):69-75. doi: 10.1126/science.aan6826.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Skene, et al. An efficient targeted nuclease strategy for high-resolution mapping of DNA binding sites. eLife. 2017; 6: e21856.
Wall, et al. "4WOR Staphylococcal nuclease in complex with Ca2+ and thymidine-3'-5'- diphosphate (pdTp) at room temperature." RCSB PDB Version 2.0 DOI: 10.2210/pdb4WOR/pdb.
Co-pending U.S. Appl. No. 17/014,909, inventor Giresi; Paul, filed Sep. 8, 2020.
Co-pending U.S. Appl. No. 17/148,942, inventors Mcdermott; Geoffrey et al., filed Jan. 14, 2021.
Co-pending U.S. Appl. No. 17/166,982, inventors Mcdermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
"Lennon et al. A scalable, fully automated process for construction of sequence-ready barcoded libraries for 454. Genome Biology 11:R15 (2010).".
Abate, A.R. et al. "Beating Poisson encapsulation statistics using close-packed ordering" Lab on a Chip (Sep. 21, 2009) 9(18):2628-2631.
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending PCT/US2019/024418, filed Mar. 27, 2019.
Co-pending PCT/US2019/046940, filed Aug. 16, 2019.
Co-pending U.S. Appl. No. 16/410,953, filed May 13, 2019.
Co-pending U.S. Appl. No. 16/415,617, filed May 17, 2019.
Co-pending U.S. Appl. No. 16/434,068, filed Jun. 6, 2019.
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,089, filed Apr. 1, 2019.
Co-pending U.S. Appl. No. 16/434,095, filed Jun. 6, 2019.
Co-pending U.S. Appl. No. 16/434,099, filed Jun. 6, 2019.
Co-pending U.S. Appl. No. 16/434,102, filed Jun. 6, 2019.
Co-pending U.S. Appl. No. 16/434,605, filed Jun. 7, 2019.
Co-pending U.S. Appl. No. 16/435,393, filed Jun. 7, 2019.
Co-pending U.S. Appl. No. 16/439,568, filed Jun. 12, 2019.
Co-pending U.S. Appl. No. 16/439,675, filed Jun. 12, 2019.
Co-pending U.S. Appl. No. 16/454,485, filed Jun. 27, 2019.
Co-pending U.S. Appl. No. 16/530,930, filed Aug. 2, 2019.
Co-pending U.S. Appl. No. 16/575,280, filed Sep. 18, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Duffy et al., Rapid Protyping of Microfluidic Systems and Polydimethylsiloxane, Anal Chem 70:4974-4984 (1998).

(56) References Cited

OTHER PUBLICATIONS

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.
Jarosz, M. et al. "Using 1ng of DNA to detect haplotype phasing and gene fusions from whole exome sequencing of cancer cell lines" Cancer Res (2015) 75(suppl5):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chern. 8: 1110-1115 (2008).
Lagally, et al. Single-Molecule DNA Amplification and Analysis in an Integrated Microfluidic Device. Anal Chem. Feb. 1, 2001;73(3):565-70.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Mccoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Pushkarev et al. "Single-molecule sequencing of an individual human genome," Nature Biotech (2009) 17:847-850.
Ramsey, J.M. "The burgeoning power of the shrinking laboratory" Nature Biotech (1999) 17:1061-1062.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. 2010. Polymer.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shendure et al. "Accurate Multiplex Polony Sequencing of an Evolved bacterial Genome" Science (2005) 309:1728-1732.
Song, et al. Reactions in droplets in microfluidic channels. Angew Chem Int Ed Engl. Nov. 13, 2006;45(44):7336-56.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)"107-121.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Co-pending U.S. Appl. No. 17/318,364, inventors Bava; Felice Alessio et al., filed May 12, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending U.S. Appl. No. 17/580,947, inventor Gibbons; Michael, filed Jan. 21, 2022.
Co-pending U.S. Appl. No. 17/831,835, inventor Martinez; Luigi Jhon Alvarado, filed Jun. 3, 2022.
Co-pending U.S. Appl. No. 17/957,781, inventor Bava; Felice Alessio, filed Sep. 30, 2022.
Co-pending U.S. Appl. No. 18/046,843, inventor Toh; Mckenzi, filed Oct. 14, 2022.

(56) References Cited

OTHER PUBLICATIONS

Co-pending U.S. Appl. No. 18/152,650, inventor Shastry; Shankar, filed Jan. 10, 2023.

* cited by examiner

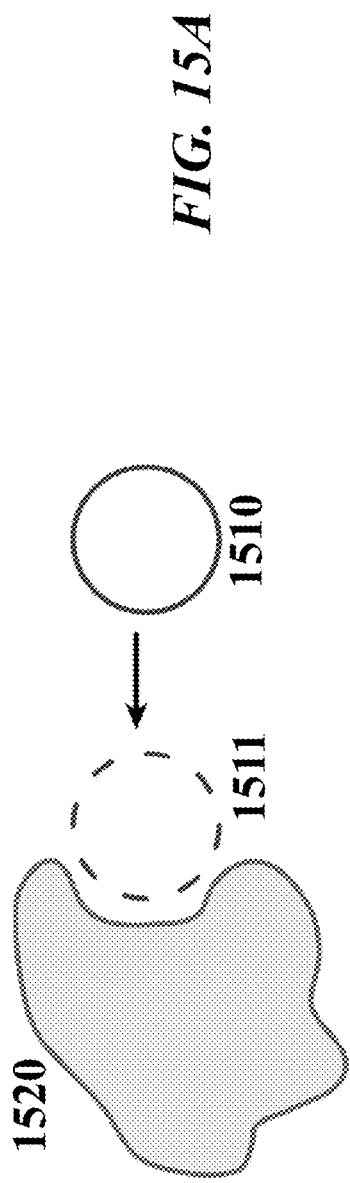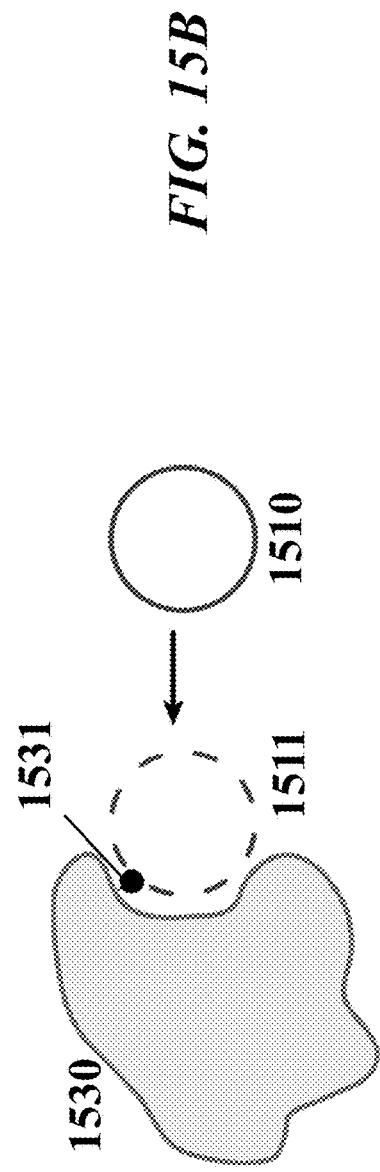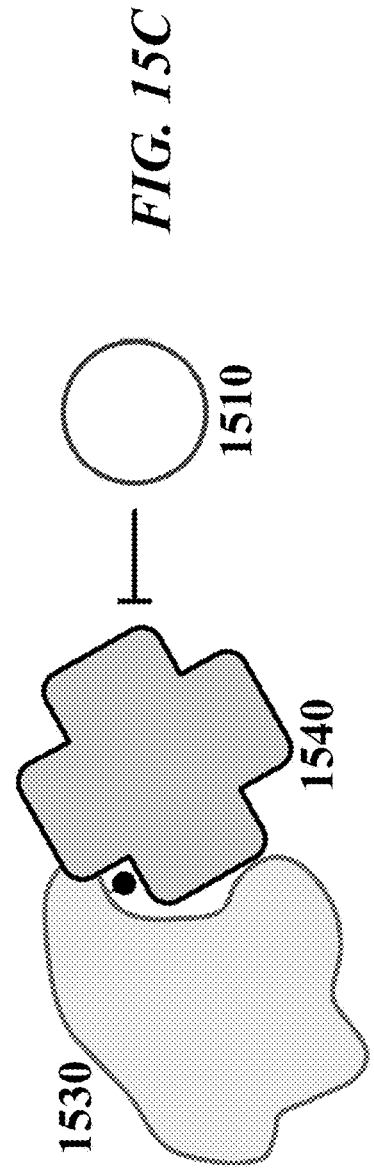

COMPOSITIONS AND METHODS FOR CELLULAR PROCESSING

CROSS-REFERENCE

This application claims the benefit of U.S. Provisional Patent Application No. 62/845,164, filed May 8, 2019, and U.S. Provisional Patent Application No. 62/720,065, filed Aug. 20, 2018, each of which applications is entirely incorporated herein by reference.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

In some aspects, the present disclosure provides a method for nucleic acid analysis, comprising: generating a partition comprising (i) a cell bead comprising a nucleic acid, (ii) a nucleic acid barcode molecule, and (iii) a polymer; and (b) using said nucleic acid or a fragment thereof and said nucleic acid barcode molecule to perform one or more reactions in said partition. In some embodiments, the partition is a droplet. In some embodiments, the partition is a well. In some embodiments, the one or more reactions are performed outside the cell bead. In some embodiments, the one or more reactions comprise nucleic acid extension. In some embodiments, the one or more reactions comprise nucleic acid amplification. In some embodiments, the method further comprises releasing the barcoded nucleic acid from the partition. In some embodiments, the cell bead or the polymer is functionalized. In some embodiments, the polymer is a charged polymer. In some embodiments, the polymer is positively charged. In some embodiments, the polymer is negatively charged. In some embodiments, the cell bead or the polymer is attached to a reagent. In some embodiments, the reagent is an enzyme, a nucleic acid molecule comprising a capture sequence, an aptamer, a chemical compound, or a polypeptide. In some embodiments, the reagent comprises biotin. In some embodiments, the reagent is a small molecule inhibitor. In some embodiments, the small molecule inhibitor is deoxythymidine 3',5'-bisphosphate. In some embodiments, the chemical compound is a chelating agent. In some embodiments, the chelating agent is ethylenediaminetetraacetic acid (EDTA) or ethylene glycol-bis (β-aminoethyl ether)-N,N,N',N'-tetraacetic acid (EGTA). In some embodiments, the capture sequence is a poly-thymine (poly-T) sequence, a random N-mer sequence, or a targeted capture sequence. In some embodiments, the enzyme is a nuclease, transposase, polymerase, helicase, reverse transcriptase, ligase, or phosphatase. In some embodiments, the nucleic acid molecule comprising the capture sequence further comprises a functional sequence selected from the group consisting of a barcode sequence, a unique molecular index (UMI) sequence, a sequencing primer sequence, a partial sequencing primer sequence, and a sequence configured to attach to the flow cell of a sequencer. In some embodiments, the partition further comprises an enzyme configured to perform the one or more reactions on the nucleic acid molecule or a derivative thereof. In some embodiments, the partition comprises a cation for activating the enzyme. In some embodiments, the cation is magnesium or calcium. In some embodiments, the method further comprises, prior to (a), contacting the cell bead with the enzyme and performing one or more reactions on the nucleic acid molecule. In some embodiments, the enzyme is a nuclease, transposase, polymerase, helicase, reverse transcriptase, ligase, or phosphatase. In some embodiments, the nuclease is micrococcal nuclease (MNase). In some embodiments, the nuclease is DNase.

In some embodiments, the method further comprises, prior to (b), using the nuclease to cleave the nucleic acid molecule to generate a nucleic acid fragment. In some embodiments, the enzyme is an engineered enzyme. In some embodiments, the engineered enzyme is an engineered nuclease. In some embodiments, the engineered nuclease comprises a binding moiety configured to bind to a binding partner. In some embodiments, binding of the binding partner to the binding moiety inhibits the engineered nuclease. In some embodiments, the binding partner is a protein. In some embodiments, the binding moiety is an aptamer. In some embodiments, the binding moiety comprises biotin. In some embodiments, the binding partner is streptavidin or avidin. In some embodiments, the one or more reactions comprises using a ligase to ligate the nucleic acid barcode molecule to the nucleic acid molecule or derivative thereof. In some embodiments, the nucleic acid barcode molecule is attached to a bead. In some embodiments, the bead comprises chemical cross-linkers. In some embodiments, the chemical cross-linkers are disulfide bonds. In some embodiments, the bead is a gel bead. In some embodiments, the nucleic acid barcode molecule is attached to the bead via a releasable linker. In some embodiments, the releasable linker is a disulfide bond. In some embodiments, the nucleic acid barcode molecule is released from the bead prior to performing the one or more reactions. In some embodiments, the polymer is a linear polymer. In some embodiments, the polymer is a branched polymer. In some embodiments, the polymer is not cross-linked. In some embodiments, the polymer is dextran, polyethylene glycol (PEG), or polyacrylamide.

In some embodiments, the partition further comprises a particle. In some embodiments, the particle is a magnetic particle. In some embodiments, the cell bead comprises the magnetic particle. In some embodiments, the particle comprises, attached thereto, a nucleic acid molecule comprising a capture sequence. In some embodiments, the capture sequence is a poly-T sequence, a random N-mer sequence, or a targeted capture sequence. In some embodiments, the polymer is incapable of diffusing into the cell bead. In some embodiments, the method further comprises, prior to (a), generating a cell bead comprising an analyte carrier comprising the nucleic acid molecule. In some embodiments, the method further comprises lysing the analyte carrier. In some embodiments, the analyte carrier is lysed prior to (a). In some embodiments, the analyte carrier is lysed subsequent to (a). In some embodiments, the analyte carrier is permeabilized. In some embodiments, the analyte carrier is permeabilized prior to (a). In some embodiments, the analyte carrier is permeabilized subsequent to (a). In some embodiments, the analyte carrier is a cell or cell nucleus.

In some aspects, described herein is a composition for nucleic acid analysis comprising a partition comprising (i) a cell bead comprising a nucleic acid molecule, (ii) a barcoded bead comprising a nucleic acid barcode molecule, and (iii) a polymer. In some embodiments, the cell bead or the polymer is attached to a reagent. In some embodiments, the reagent is an enzyme, a nucleic acid molecule comprising a capture sequence, a chemical compound, a chelating agent, or a polypeptide. In some embodiments, the reagent comprises biotin. In some embodiments, the reagent is a small molecule inhibitor. In some embodiments, the small molecule inhibitor is deoxythymidine 3',5'-bisphosphate. In some embodiments, the chelating agent is EDTA or EGTA. In some embodiments, the nucleic acid molecule comprising the capture sequence further comprises a functional sequence selected from the group consisting of a barcode sequence, a unique molecular index (UMI) sequence, a sequencing primer sequence, a partial sequencing primer sequence, and a sequence configured to attach to the flow cell of a sequencer. In some embodiments, the capture sequence is a poly-T sequence, a random N-mer sequence, or a targeted capture sequence. In some embodiments, the partition further comprises an enzyme configured to perform the one or more reactions on the nucleic acid molecule or a derivative thereof. In some embodiments, the partition further comprises a cation for activating the enzyme. In some embodiments, the cation is magnesium or calcium. In some embodiments, the enzyme is a nuclease, a transposase, a polymerase, a helicase, a reverse transcriptase, a ligase, or a phosphatase. In some embodiments, the enzyme is a nuclease. In some embodiments, the nuclease is MNase. In some embodiments, the nuclease is DNase. In some embodiments, the enzyme is an engineered enzyme. In some embodiments, the engineered enzyme is an engineered nuclease. In some embodiments, the engineered nuclease is an engineered MNase. In some embodiments, the engineered nuclease comprises a binding moiety configured to bind to a binding partner. In some embodiments, the binding partner is a protein. In some embodiments, the binding protein is an aptamer. In some embodiments, the binding moiety comprises biotin. In some embodiments, the binding partner is streptavidin or avidin. In some embodiments, the polymer is incapable of diffusing into the cell bead. In some embodiments, the polymer is a linear polymer. In some embodiments, the polymer is a branched polymer. In some embodiments, the polymer is not cross-linked. In some embodiments, the polymer is dextran, polyethylene glycol (PEG), or polyacrylamide. In some embodiments, the partition further comprises a particle. In some embodiments, the particle is a magnetic particle. In some embodiments, the cell bead comprises the magnetic particle. In some embodiments, the particle comprises, attached thereto, a nucleic acid molecule comprising a capture sequence. In some embodiments, the capture sequence is a poly-T sequence, a random N-mer sequence, or a targeted capture sequence. In some embodiments, the cell bead comprises a lysed analyte carrier. In some embodiments, the cell bead comprises a permeabilized analyte carrier. In some embodiments, the analyte carrier is a cell or cell nucleus.

Disclosed herein, in some aspects, is a method for generating a barcoded nucleic acid, comprising: (a) generating a cell bead comprising a permeabilized nucleus and a nuclease; (b) co-partitioning (i) the cell bead, (ii) a nucleic acid barcode molecule, and (iii) a polymer comprising an inhibitor of the nuclease into a partition; (c) using the nuclease to fragment a nucleic acid from the nucleus, thereby generating a nucleic acid fragment; (d) releasing (i) the nucleic acid fragment and (ii) the nuclease from the cell bead, thereby inhibiting the nuclease with the inhibitor; and (e) using the nucleic acid fragment and the nucleic acid barcode molecule to generate the barcoded nucleic acid. In some embodiments, the nuclease is attached to a binding moiety. In some embodiments, the nuclease is attached to the binding moiety via a binding protein. In some embodiments, the nuclease is attached to the binding protein via a linker. In some embodiments, the binding protein is Protein A or Protein G. In some embodiments, the nuclease is attached to the binding moiety via a linker. In some embodiments, the binding moiety is an antibody or antibody fragment. In some embodiments, the method further comprises releasing the barcoded nucleic acid molecule from the partition. In some embodiments, the method further comprises sequencing the barcoded nucleic acid molecule. In some embodiments, the partition further comprises a particle. In some embodiments, the particle is a magnetic particle. In some embodiments, the particle comprises, attached thereto, a nucleic acid molecule comprising a capture sequence. In some embodiments, the capture sequence is a poly-T sequence, a random N-mer sequence, or a targeted capture sequence. In some embodiments, the partition further comprises a bead. In some embodiments, the bead comprises chemical cross-linkers. In some embodiments, the chemical cross-linkers are disulfide bonds. In some embodiments, the bead is a gel bead. In some embodiments, the nucleic acid barcode molecule is attached to the bead. In some embodiments, the nucleic acid barcode molecule is attached to the bead via an acrydite moiety. In some embodiments, the nucleic acid barcode molecule is attached to the bead via a releasable linker. In some embodiments, the releasable linker is a disulfide bond. In some embodiments, the nucleic acid barcode molecule is released from the bead prior to (e).

In some embodiments, the polymer is a linear polymer. In some embodiments, the polymer is a branched polymer. In some embodiments, the polymer is not cross-linked. In some embodiments, the polymer is dextran, polyethylene glycol (PEG), or polyacrylamide. In some embodiments, the polymer is incapable of diffusing into the cell bead. In some embodiments, the inhibitor is an enzyme, a nucleic acid molecule comprising a capture sequence, a chemical compound, a chelating agent, or a polypeptide. In some embodiments, the inhibitor comprises biotin. In some embodiments, the inhibitor is a small molecule inhibitor. In some embodiments, the small molecule inhibitor is deoxythymidine 3',5'-bisphosphate. In some embodiments, the chelating agent is EDTA or EGTA. In some embodiments, the nuclease is an engineered nuclease. In some embodiments, the engineered nuclease is an engineered MNase. In some embodiments, the engineered nuclease is an engineered DNase. In some embodiments, the engineered nuclease comprises a binding moiety configured to bind to a binding partner. In some embodiments, the binding partner is a protein. In some embodiments, the binding partner is an aptamer. In some embodiments, the binding moiety comprises biotin. In some embodiments, the binding partner is streptavidin or avidin. In some embodiments, the polymer is incapable of diffusing into the cell bead. In some embodiments, the partition comprises a cation for activating the nuclease. In some embodiments, the cation is magnesium or calcium.

In some aspects, present disclosure provides a composition for nucleic acid analysis comprising a partition comprising (i) a cell bead comprising a nucleic acid, (ii) a barcoded bead comprising a nucleic acid barcode molecule, and (iii) a polymer.

In some aspects, present disclosure provides a method for generating a barcoded nucleic acid, comprising: (a) generating a cell bead comprising a permeabilized nucleus and a nuclease; (b) co-partitioning (i) said cell bead, (ii) a nucleic acid barcode molecule, and (iii) a polymer comprising an inhibitor of said nuclease into a partition; (c) using said nuclease to fragment a nucleic acid from said nucleus, thereby generating a nucleic acid fragment; (d) releasing (i) said nucleic acid fragment and (ii) said nuclease from said cell bead into said partition, thereby inhibiting said nuclease; and (e) releasing (i) said nucleic acid fragment and (ii) said nuclease from said cell bead into said partition, thereby inhibiting said nuclease.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 15A-C illustrates an example method for inhibiting an engineered enzyme.

DETAILED DESCRIPTION

Figure 1:
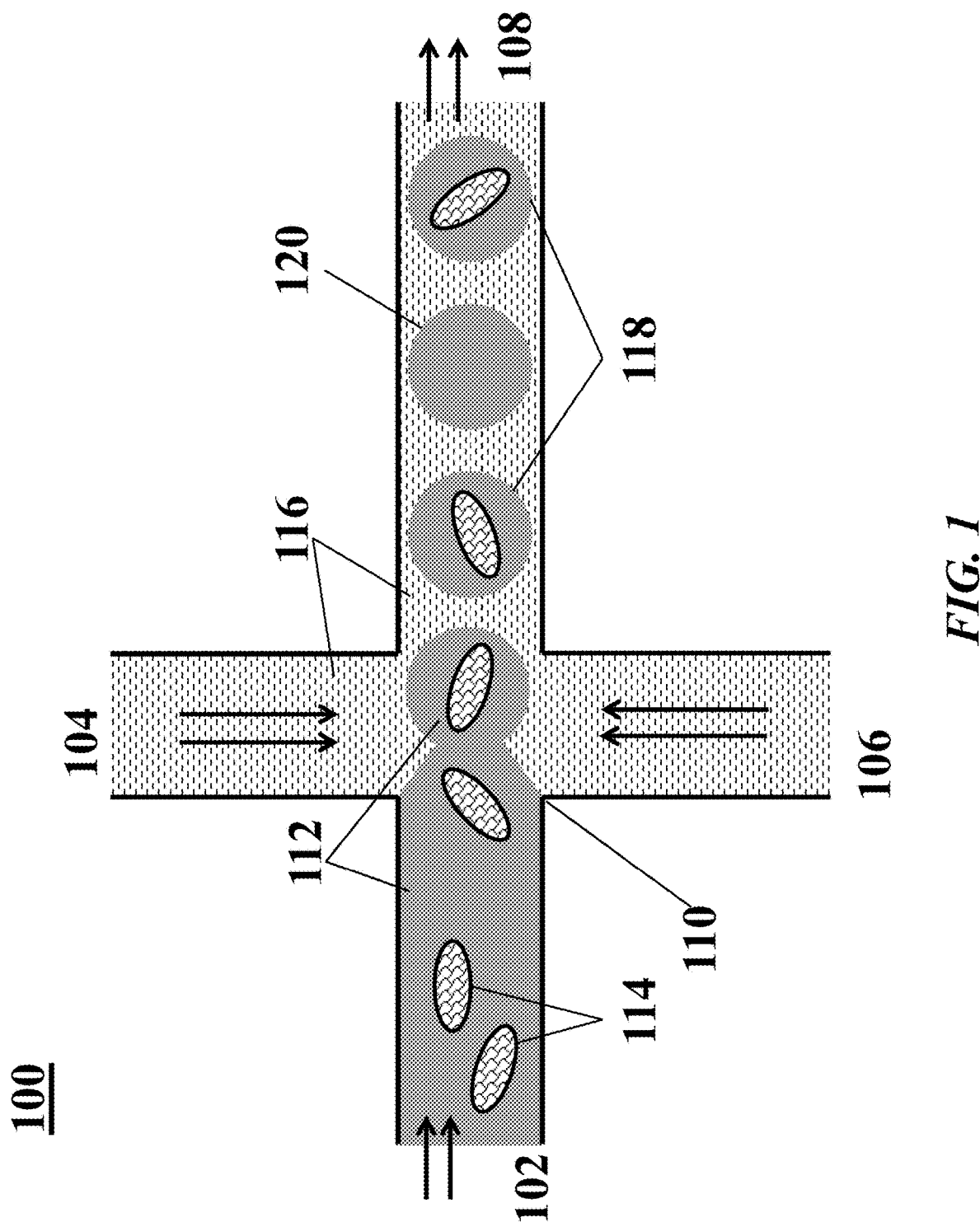
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The terms "biological particle" or "analyte carrier," as used herein, generally refers to a discrete biological system derived from a biological sample. The biological particle or analyte carrier may comprise, or carry therein, an analyte (e.g., biological analyte) of interest. In some embodiments, the analyte carrier is itself the analyte of itnerset. The biological particle or analyte carrier may be a virus. The biological particle or analyte carrier may be a cell or derivative of a cell. The biological particle or analyte carrier may be an organelle. The biological particle or analyte carrier may be a rare cell from a population of cells. The biological particle or analyte carrier may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle or analyte carrier may be a constituent of a cell. The biological particle or analyte carrier may be or may include DNA, RNA, organelles, proteins, or any combination thereof. The biological particle or analyte carrier may be or may include a matrix (e.g., a gel or polymer matrix) comprising a cell or one or more constituents from a cell (e.g., cell bead), such as DNA, RNA, organelles, proteins, or any combination thereof, from the cell. The biological particle or analyte carrier may be obtained from a tissue of a subject. The biological particle or analyte carrier may be a hardened cell. Such hardened cell may or may not include a cell wall or cell membrane. The biological particle or analyte carrier may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix. As used herein, the terms "biological particle" and "analyte carrier" may be used interchangeably.

The term "cell bead," as used herein, generally refers to a particle that comprises (e.g., encapsulates, contains, attaches to, immobilizes to, etc.) a biological particle or analyte carrier (e.g., a cell, a nucleus, a fixed cell, a cross-linked cell), a virus, components of, or macromolecular constituents derived from a cell or virus. A cell bead may comprise a hydrogel, polymeric, or crosslinked material. For example, a cell bead may comprise a virus and/or a cell. In some cases, a cell bead comprises a single cell. In some cases, a cell bead may comprise multiple cells adhered together. A cell bead may include any type of cell, including without limitation prokaryotic cells, eukaryotic cells, bacterial, fungal, plant, mammalian, or other animal cell types, mycoplasmas, normal tissue cells, tumor cells, a T-cell (e.g., CD4 T-cell, CD4 T-cell that comprises a dormant copy of human immunodeficiency virus (HIV)), a fixed cell, a cross-linked cell, a rare cell from a population of cells, or any other cell type, whether derived from single cell or multicellular organisms. Furthermore, a cell bead may comprise a live cell, such as, for example, a cell capable of being cultured. Moreover, in some examples, a cell bead may comprise a derivative of a cell, such as one or more components of the cell (e.g., an organelle, a cell protein, a cellular nucleic acid, genomic nucleic acid, messenger ribonucleic acid, a ribosome, a cellular enzyme, etc.). In some examples, a cell bead may comprise material obtained from a biological tissue, such as, for example, obtained from a subject. In some cases, cells, viruses or macromolecular constituents thereof are encapsulated within a cell bead. Encapsulation can be within a polymer or gel matrix that forms a structural component of the cell bead. In some cases, a cell bead is generated by fixing a cell in a fixation medium or by cross-linking elements of the cell, such as the cell membrane, the cell cytoskeleton, etc. In some cases, beads may or may not be generated without encapsulation within a larger cell bead.

The term "macromolecular constituent," as used herein, generally refers to a macromolecule contained within or from a biological particle or analyte carrier. The macromolecular constituent may comprise a nucleic acid. In some cases, the biological particle or analyte carrier may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "antigen binding fragment," "epitope binding fragment," or "antibody fragment," as used herein, generally refers to a portion of an antibody (e.g., comprising each domain of the light and heavy chains respectively) capable of binding the same epitope/antigen as the antibody. In some instances, such a fragment may bind, be configured to bind, or be capable of binding the same epitope or antigen as the antibody to the same extent. In some instances, such a fragment may bind, be configured to bind, or be capable of binding the same epitope or antigen as the antibody to a lesser extent Although multiple types of epitope binding fragments are possible, an epitope binding fragment typically comprises at least one pair of heavy and light chain variable regions (VH and VL, respectively) held together (e.g., by disulfide bonds) to preserve the antigen binding site and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an $F(ab')_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Cellular Compositions

Cell beads may be used to trap high molecular weight material (e.g., genomic DNA), while remaining permeable to small molecules and enzymes. Cell beads may be partitioned into partitions (e.g., droplets, wells). Within these partitions, it may be difficult or impossible to temporally phase a chemical or biochemical reaction through the sequential addition of an activating or inhibitory agent, which may be required to generate a particular product. For example, it may be desirable to release either original fragments of genomic material, or copies of those fragments, from a cell bead through the use of an enzyme, such as a nuclease, transposase, polymerase or reverse transcriptase. In some applications, it is important to spatially partition the activity of the enzyme. For example, in an application where fragments of genomic material are excised from the genome using a nuclease, it may be desirable to spatially control the activity of the nuclease so that it may only function inside the cell bead within a partition where competing enzymatic activities may be acting on molecular targets. Alternatively, it may be desirable to capture target molecules such as poly-A tailed mRNA or ribosomal RNA (rRNA) that diffuse from the cell bead within the GEM. Disclosed herein are methods and compositions for spatially partitioning molecules (e.g., RNA, DNA, protein, small molecules, etc) inside a partition (e.g., a droplet).

In an aspect, provided herein are compositions for nucleic acid analysis. A composition may comprise a partition comprising a cell bead, a barcoded bead, and a polymer. A partition may be a droplet. A cell bead may comprise a cell. A cell bead may comprise a nucleus. A cell bead may comprise a permeabilized nucleus. A polymer may be incapable of diffusing into a cell bead. A polymer may be a functionalized polymer (e.g., may comprise one or more functional components). A polymer may be a linear polymer. A polymer may be a branched polymer. A polymer may be attached to a reagent. A reagent may be, for example, an enzyme, a nucleic acid, a chemical compound, or a protein. A polymer may be functionalized with a chemical compound. A chemical compound may be an inhibitor of an enzyme. A chemical compound may be, for example, deoxythymidine 3',5'-bisphosphate or ethylene glycol-bis(β-aminoethyl ether)-N,N,N',N'-tetraacetic acid (EGTA). A polymer may be functionalized with a charged species. A polymer may comprise an oligonucleotide comprising a capture sequence. A capture sequence may be a polyT sequence, a random sequence, or an rRNA capture sequence. A partition may comprise a particle (e.g., a magnetic particle).

A partition (e.g., droplet) may comprise an enzyme. An enzyme may be, for example, a nuclease, transposase, polymerase, helicase, reverse transcriptase, ligase, or phosphatase. In some cases, an enzyme is a nuclease. A nuclease may be a micrococcal nuclease (MNase) or a DNase. An enzyme may be an engineered enzyme. An engineered enzyme may be an engineered nuclease. An engineered enzyme may comprise a ligand attached thereto. A ligand may be, for example, biotin. An engineered nuclease may be modified with a ligand such that, upon binding of a ligand-binding protein to the ligand, the enzyme is inactivated.

An enzyme may be attached to a binding moiety. A binding moiety may be an antibody or fragment thereof. An enzyme may be attached to a binding moiety directly (e.g., covalently). An enzyme may be attached to a binding moiety indirectly (e.g., non-covalently). An enzyme may be attached to a binding protein (e.g., Protein A, Protein G). An enzyme may be attached to a binding moiety via a binding protein. A binding moiety may be capable of binding to a nucleic acid binding protein (e.g., transcription factor, histone, etc.). A partition may comprise one or more cations for activating an enzyme. Examples of cations include magnesium ($Mg^{2+}$) and calcium ($Ca^{2+}$).

Figure 9:
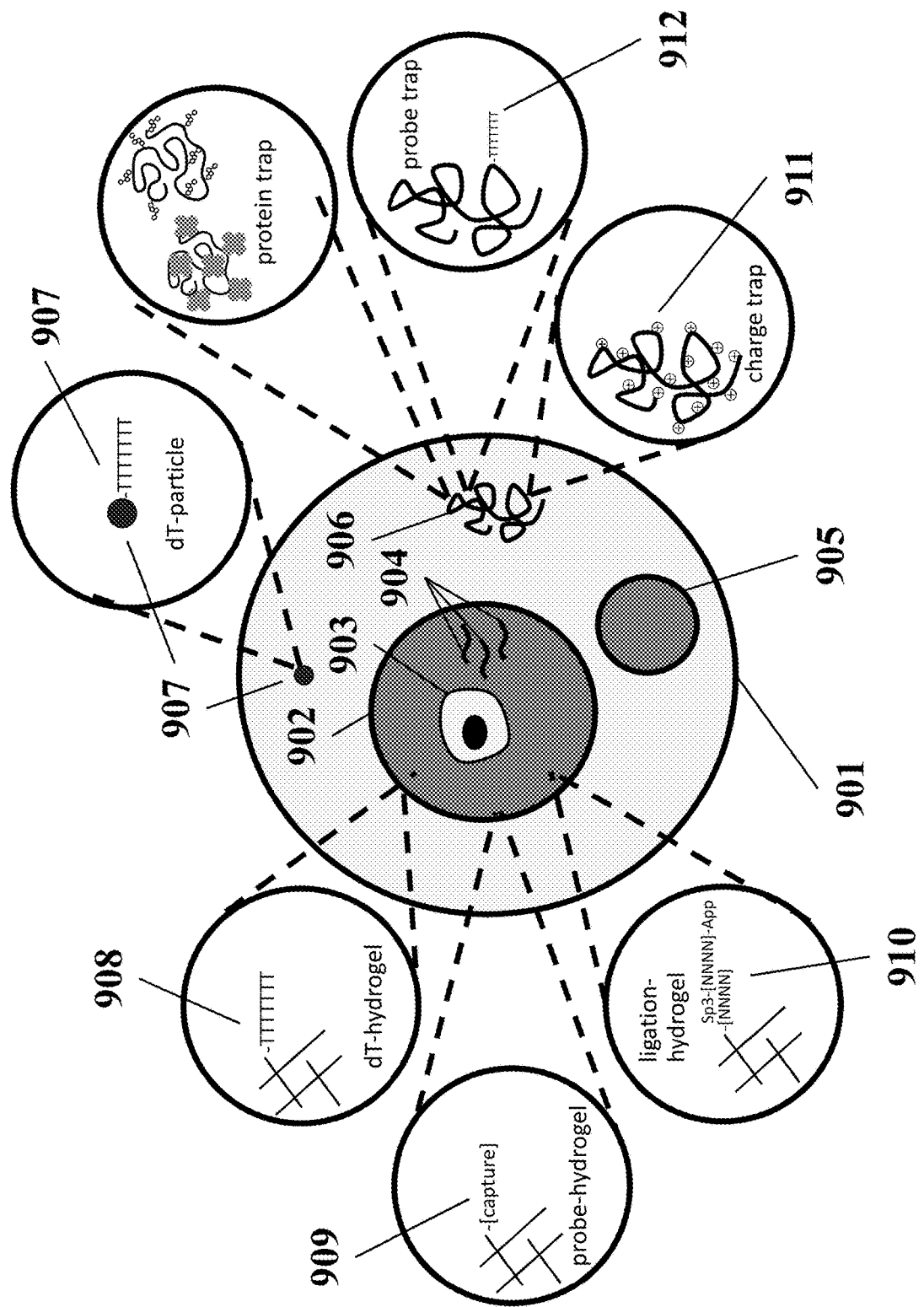
FIG. 9 shows a diagram of methods for capturing molecules in or around a cell bead in a droplet.

FIG. 9 shows examples of compositions for nucleic acid analysis. For instance, in some embodiments, partition 901, such as a droplet in an emulsion or a well (e.g., in a microwell array), comprises cell bead 902 comprising analyte carrier or biological particle 903 (e.g., a cell or nucleus) and/or nucleic acids derived from a cell 904. In some instances, cell bead 902 comprises a polymeric or cross-linked matrix (e.g., a hydrogel) that comprises one or more functional moieties or groups. For example, the cell bead polymeric or cross-linked matrix ("cell bead matrix") may comprise one or more nucleic acid molecules. The one or more nucleic acid molecules may comprise one or more functional sequences (e.g., 908, 909, and/or 910) configured to facilitate one or more interactions or reactions with a component (e.g., a cellular nucleic acid) of partition 901. For example, in some instances, the cell bead matrix comprises a nucleic acid molecule comprising a poly-T sequence 908, such as the poly-T sequences described elsewhere herein. A poly-T sequence may be useful in, for example, capturing mRNA from a sample (e.g., a cell) and/or generating cDNA from mRNA. In other embodiments, the cell bead matrix comprises a nucleic acid molecule comprising a capture sequence 909 configured to hybridize and/or couple to, e.g., a complementary or partially complementary nucleic acid sequence. A capture sequence 909 may be, for example, a random nucleotide sequence or an rRNA capture sequence. In other instances, a capture sequence 909 can be a targeted sequence, such as a sequence configured to be complementary to a cellular nucleic acid, such as a specific mRNA and/or genomic DNA sequence. In still other embodiments, the cell bead matrix comprises a nucleic acid molecule comprising a chemical modification 910 (e.g., 5'-adenylation) configured to enable covalent capture (e.g., ligation) of a second nucleic acid molecule. The cell bead matrix may also comprise nucleic acid molecules comprising other functional nucleic acid sequences, such as a barcode sequence, a unique molecular index (UMI) sequence, a sequencing primer sequence (or a partial sequencing primer sequence, such as a partial R1 and/or R2 sequence), and/or one or more adaptor sequences, such as a sequence configured to attach to the flow cell of a sequencer (e.g., P5, P7), etc. These sequences may be, in some instances, in addition to the functional sequences described above (e.g., 908, 909, and/or 910).

Partition 901 (e.g., a droplet) may further comprise bead 905. Bead 905 may be a bead as described elsewhere herein (see, for example, FIG. 8). Bead 905 may be a gel bead. In some instances, bead 905 comprises one or more nucleic acid barcode molecules (e.g., is a barcoded bead) as described in greater detail elsewhere herein. Nucleic acid barcode molecules may be attached (e.g., releasably attached) to bead 905.

Partition 901 may further comprise a polymer 906. Polymer 906 may be a linear polymer. Polymer 906 may be a branched polymer. In some instances, polymer 906 is a high molecular weight (HMW) polymer. For example, polymer 906 may comprise dextran, polyethylene glycol (PEG), polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, elastin, a polyolefin, an olefin copolymers, an acrylics, a vinyl polymer, a polyesters, a polycarbonate, a polyamide, a polyimide, a formaldehyde resin, a polyurethane, an ether polymer, a cellulosic, a thermoplastic elastomer, a thermoplastic polyurethane, or any polymeric precursor (e.g., monomer) thereof. In some instances, polymer 906 is configured such that polymer 906 is incapable of diffusing into cell bead 902. In some instances, polymer 906 is a functionalized polymer. A functionalized polymer may be useful in spatially partitioning reactions within partition 901. For example, polymer 906 may be functionalized with, e.g., a protein or polypeptide, a chemical compound (e.g., a small molecule), or other functionalized group attached thereto. A protein, polypeptide, or chemical compound attached to polymer 906 may be useful in, for example, selectively inhibiting an enzyme (e.g., following release from cell bead 902) or otherwise sequestering a species in partition 901. A protein, polypeptide, or chemical compound may be covalently attached to polymer 906. A protein, polypeptide, or chemical compound may be non-covalently or indirectly attached to polymer 906, e.g., through functional groups attached to polymer 906. The protein, polypeptide, or chemical compound attached to polymer 906 may be capable of binding one or more specific ligands. For example, in some embodiments, polymer 906 comprises streptavidin or a polypeptide capable of binding biotin. In some instances, polymer 906 comprises a biotin moiety. In some instances, the chemical compound attached to polymer 906 may be an inhibitor of an enzyme. For example, in some embodiments, deoxythymidine 3',5'-bisphosphate is attached to polymer 906, thereby inhibiting, e.g., a nuclease, such as micrococcal nuclease (MNase). In another example, polymer 906 is functionalized with a chelation agent such as ethylene glycol-bis(β-aminoethyl ether)-N,N,N',N'-tetraacetic acid (EGTA) or ethylenediaminetetraacetic acid (EDTA), thereby chelating one or more cofactors present in partition 901.

Polymer 906 may comprise one or more nucleic acid molecules. The one or more nucleic acid molecules may comprise one or more functional sequences (e.g., the functional sequences 908, 909, and/or 910 described above) configured to facilitate one or more interactions or reactions with a component (e.g., a cellular nucleic acid) of partition 901. For example, in some instances, the polymer 906 comprises a nucleic acid molecule comprising a poly-T sequence 912, such as the poly-T sequences described elsewhere herein. In other embodiments, polymer 906 comprises a nucleic acid molecule comprising a capture sequence (similar to capture sequence 909) configured to hybridize and/or couple to a nucleic acid sequence, e.g., a complementary or partially complementary nucleic acid sequence. A capture sequence may be, for example, a random nucleotide sequence or an rRNA capture sequence. In other instances, a capture sequence can be a targeted sequence, such as a sequence configured to be complementary to a cellular nucleic acid, such as a specific mRNA and/or genomic DNA sequence. In still other embodiments, polymer 906 comprises a nucleic acid molecule comprising a chemical modification (e.g., 5'-adenylation as depicted in 910) configured to enable covalent capture (e.g., ligation) of a second nucleic acid molecule. Polymer 906 may also comprise nucleic acid molecules comprising other functional nucleic acid sequences, such as a barcode sequence, a unique molecular index (UMI) sequence, a sequencing primer sequence (or a partial sequencing primer sequence, such as a partial R1 and/or R2 sequence), and/or one or more adaptor sequences, such as a sequence configured to attach to the flow cell of a sequencer (e.g., P5, P7), etc. These sequences may be, in some instances, in addition to the functional sequences described above (e.g., 908, 909, and/or 910).

Polymer 906 may be a charged polymer or comprise one or more charged functional groups. Polymer 906 may be positively charged. Polymer 906 may be negatively charged. A charged polymer may be useful in, for example, capturing analytes (e.g., one or more cellular components) of opposite charge. For example, polymer 906 may be a positively charged polymer 911, thereby capturing negatively charged nucleic acid molecules released from a cell bead.

Partition 901 (e.g., an aqueous droplet) may further comprise a particle 907. Particle 907 may be a magnetic particle. Particle 907 may be a paramagnetic particle. Particle 907 may be a bead (e.g., a magnetic bead). Particle 907 may be associated with, or otherwise embedded within, e.g., cell bead 902, bead 905 (e.g., a gel bead), and/or polymer 906. Particle 907 may be separate from cell bead 902, bead 905 (e.g., a gel bead), and polymer 906 (e.g., contained within an aqueous portion of partition 901). Particle 907 may be comprised within one or more of cell bead 902, bead 905 (e.g., a gel bead), polymer 906, and/or within an aqueous portion of partition 901.

Particle 907 may comprise one or more nucleic acid molecules. The one or more nucleic acid molecules may comprise one or more functional sequences (e.g., the functional sequences 908, 909, and/or 910 described above) configured to facilitate one or more interactions or reactions with a component (e.g., a cellular nucleic acid) of partition 901. For example, in some instances, particle 907 comprises a nucleic acid molecule comprising a poly-T sequence (similar to poly-T sequences 908 and 912). In other embodiments, particle 907 comprises a nucleic acid molecule comprising a capture sequence (similar to capture sequence 909) configured to hybridize and/or couple to, e.g., a complementary or partially complementary nucleic acid sequence. A capture sequence may be, for example, a random nucleotide sequence or an rRNA capture sequence. In other instances, a capture sequence can be a targeted sequence, such as a sequence configured to be complementary to a cellular nucleic acid, such as a specific mRNA and/or genomic DNA sequence. In still other embodiments particle 907 comprises a nucleic acid molecule comprising a chemical modification (e.g., 5'-adenylation as depicted in 910) configured to enable covalent capture (e.g., ligation) of a second nucleic acid molecule. Particle 907 may also comprise nucleic acid molecules comprising other functional nucleic acid sequences, such as a barcode sequence, a unique molecular index (UMI) sequence, a template switching oligonucleotide (TSO) sequence (such as those described elsewhere herein), a sequencing primer sequence (e.g., a R1 and/or R2 sequence or a partial sequencing primer sequence, such as a partial R1 and/or R2 sequence), and/or one or more adaptor sequences, such as a sequence configured to attach to the flow cell of a sequencer (e.g., P5, P7), etc. These sequences may be, in some instances, in addition to the functional sequences described above (e.g., 908, 909, and/or 910).

In some embodiments, the nucleic acid molecules attached to, e.g. cell bead 902 or polymer 906, are single-stranded nucleic acid molecules. In some embodiments, the nucleic acid molecules attached to, e.g. cell bead 902 or polymer 906, are double-stranded nucleic acid molecules. In some embodiments, the nucleic acid molecules attached to, e.g. cell bead 902 or polymer 906, are partially double-stranded nucleic acid molecules.

In some cases, the length of a nucleic acid molecule attached to, e.g. cell bead 902 or polymer 906, is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a nucleic acid molecule attached to, e.g. cell bead 902 or polymer 906, is at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a nucleic acid molecule attached to, e.g. cell bead 902 or polymer 906, is at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Generation of Functionalized Polymers

Cell beads (or polymer 906) comprising a nucleic acid molecule attached thereto can be generated using any suitable method(s) described herein. For a description of cell beads and cell bead generation strategies, see U.S. Pat. Pub. US 2018/0216162 and PCT Application PCT/US18/54458, filed Oct. 4, 2018, both of which are hereby incorporated by reference in their entirety. For example, in some embodiments, an analyte carrier (e.g., a cell or cell nucleus) is partitioned into a partition (e.g., a droplet in an emulsion) with polymeric or gel precursors and one or more nucleic acid molecules comprising, e.g., one or more functional sequences, such as the functional sequences described elsewhere herein (e.g., 908, 909, and/or 910). The partition is subjected to conditions sufficient to polymerize or cross-link the polymeric or gel precursors to generate the cell bead, wherein the cell bead encapsulates the analyte carrier and the one or more nucleic acid molecules.

In some cases, cell beads (or polymer 906) can be synthesized in one-step procedures, e.g., polymerization and concurrent cross-linking reactions of multifunctional monomers. In other cases, cell beads can be synthesized in multi-steps procedures, e.g., polymerization of monomers first, followed by crosslinking reactions by using, e.g., orthogonal, reactive groups that can respond to different conditions to allow stepwise approaches.

Cell beads (or polymer 906) can be synthesized by techniques that can create a crosslinked polymer. In some cases, copolymerization/cross-linking free radical polymerizations can be used to produce hydrogels by reacting hydrophilic monomers with multifunctional crosslinking molecules. This can be done by, for example, linking polymer chains via a chemical reaction(s), using ionizing radiation to generate main-chain free radicals which can recombine as crosslinking junctions, or physical interactions such as entanglements, electrostatics, and crystallite formation. Types of polymerization can include bulk, solution, and suspension polymerization.

Suspension polymerization or dispersion polymerization can be employed in water-in-oil or emulsion processes, sometimes called "inversion suspension." In some cases, the monomers and initiators can be dispersed in the oil or hydrocarbon phase as a homogenous mixture. In some cases, two types of polymer molecules can be first produced, each having a reactive, crosslinking moiety for cross-linking purposes. Then these two types of polymer molecules can be enclosed in an emulsion such that the two reactive, cross-linking moieties can react and form crosslinks between the two types of polymers, thereby completing the synthesis of the hydrogel.

In some cases, cell beads (or polymer 906) can be synthesized from monomers, polymerization initiators, and crosslinking reagents. After the polymerization reactions are complete, the hydrogels formed can be separated from remaining starting materials, unwanted by-products, etc. The length of the polymer formed can be controlled depending on the desired properties of the hydrogels.

Types of polymerizations employed to synthesize hydrogels can include, but are not limited to, free radical polymerization, controlled radical polymerization, crosslinking polymerization, networks formation of water-soluble polymers, and radiation crosslinking polymerization, etc. Polymerization can be initiated by initiators or free-radical generating compounds, such as, for example, benzoyl peroxide, 2,2-azo-isobutyronitrile (AIBN), and ammonium peroxodisulphate, or by using UV-, gamma- or electron beam-radiation.

Figure 10:
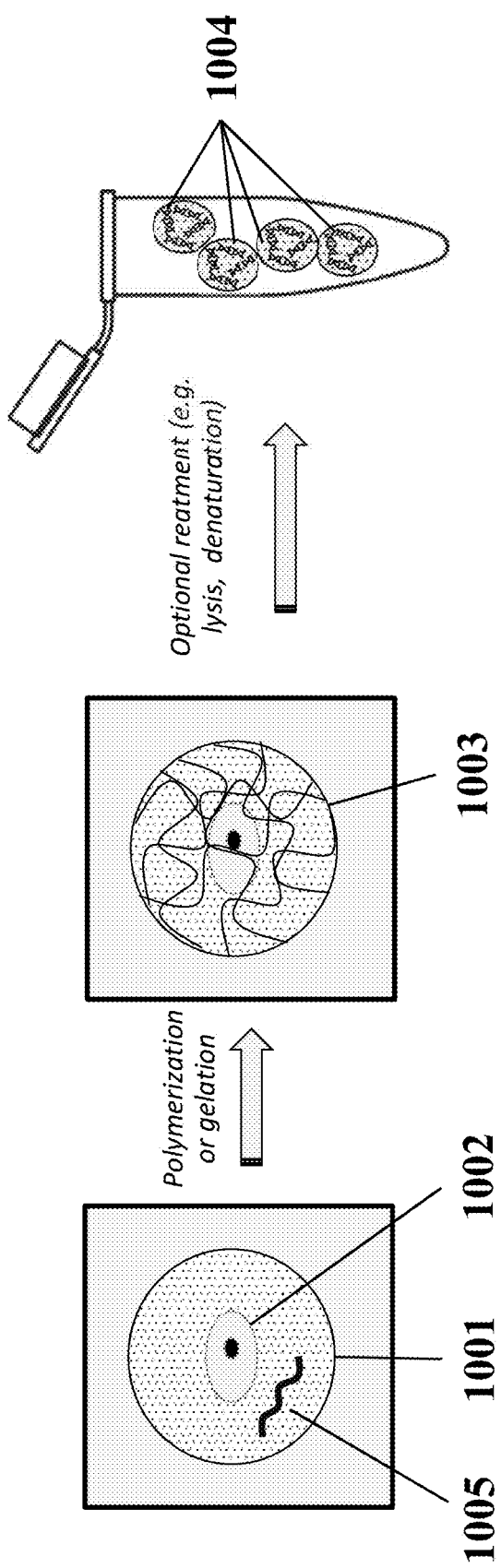
FIG. 10 illustrates an exemplary scheme for cell bead generation.

For example, as shown in FIG. 10, cells and polymer or gel precursors are mixed with an immiscible fluid (e.g., an oil), thereby generating a plurality of aqueous droplets, including droplet 1001 comprising an analyte carrier, in this instance a cell 1002. Droplet 1001 may also comprise a nucleic acid molecule comprising a functional sequence 1005, as described elsewhere herein. Droplet 1001 is subjected to conditions sufficient for polymerization or gelation of the polymer or gel precursors to generate a cell bead 1003 comprising cell 1002 and nucleic acid molecule 1005. Gelation may comprise any of the gelation mechanisms and polymers described herein. In some instances, cell bead 1003 is subjected to treatment conditions sufficient to lyse cell 1002, releasing components of the cell into the cell bead. In other embodiments, cell 1002 is lysed in droplet 1001 prior to polymerization or gelation of the polymer or gel precursors to generate cell bead 1003 comprising nucleic acid molecule 1005. In still other embodiments, cell 1002 is permeabilized before, during, or after polymerization or gelation of the polymer or gel precursors. Cell beads are collected to generate a plurality of cell beads 1004. Cell beads may be stored for further processing. In some cases, nucleic acid molecule 1005 may be attached to the cell beads subsequent to polymerization or gelation of the polymer or gel precursor. For instance, polymer or gel precursors may comprise one or more functional groups that facilitate the attachment of nucleic acid molecule 1005 subsequent to polymerization or gelation of the polymer or gel precursors. In other embodiments, the polymer or gel precursors and/or nucleic acid molecule 1005 comprise functional groups, which facilitate the incorporation of nucleic acid molecule 1005 into the cell bead during polymerization or gelation of the polymer or gel precursors.

In some embodiments, the functionalized nucleic acid molecule(s) 1005 are entrapped within the cell bead polymeric and/or crosslinked matrix (also referred to herein as a "cell bead matrix"). In other embodiments, the nucleic acid molecule(s) 1005 are functionalized with chemical groups (e.g., acrydite, amine, thiol, etc.) such that the nucleic acid molecule(s) 1005 are incorporated into or otherwise attached to the cell bead matrix. For example, in a cell bead matrix comprising polyacrylamide, the nucleic acid molecule 1005 can comprise an acrydite moiety such that, upon polymerization of acrylamide monomers, the functionalized nucleic acid molecule(s) 1005 are incorporated into the cell bead matrix. In some embodiments, both the nucleic acid molecule 1005 and/or the cell bead matrix comprise one or more functional groups configured to facilitate attachment of the nucleic acid molecule 1005 to the cell bead matrix. For example, in some embodiments, generation of a cell bead comprising a nucleic acid molecule 1005 comprises: (a) providing a plurality of polymer or gel precursors (e.g., in a partition), wherein the polymer or gel precursors comprise a plurality of first crosslink precursors; (b) providing a plurality of functionalized nucleic acid molecules comprising a second crosslink precursor; and (c) crosslinking the polymer or gel precursors and the nucleic acid molecules via a reaction between a first section of the first crosslink precursors and a second section of the second crosslink precursors, thereby forming the cell bead comprising the nucleic acid molecule(s).

In some instances, the functionalized nucleic acid molecules are irreversibly incorporated into the cell bead matrix. In other instances, the functionalized nucleic acid molecules are reversibly incorporated into the cell bead matrix. For example, a functionalized nucleic acid molecule can be functionalized with a labile moiety as described elsewhere herein (e.g., a disulfide bond) such that the functionalized nucleic acid molecule, or a portion thereof, is configured to be released from the cell bead matrix and/or cell bead.

In some embodiments, the cell bead matrix includes one or more of the following; disulfide crosslinked polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, elastin, a polyolefin, an olefin copolymers, an acrylics, a vinyl polymer, a polyesters, a polycarbonate, a polyamide, a polyimide, a formaldehyde resin, a polyurethane, an ether polymer, a cellulosic, a thermoplastic elastomer, a thermoplastic polyurethane, or any polymeric precursor (e.g., monomer) thereof. In some embodiments, the cell bead matrix comprises polyacrylamide (e.g., disulfide crosslinked polyacrylamide).

In some embodiments, generation of the cell bead matrix comprises (a) providing a first polymer or gel precursor, wherein the first polymer or gel precursor comprises a plurality of first crosslink precursors, for example a moiety comprising an azide group; (b) providing a second polymer or gel precursor, wherein the second polymer or gel precursor comprises a plurality of second crosslink precursors, for example a moiety comprising an alkyne group; and (c) crosslinking the first polymer and the second polymer via a reaction (e.g., a click-chemistry reaction) between a first section of the first crosslink precursors and a second section of the second crosslink precursors, thereby forming the cell bead.

Figure 11:
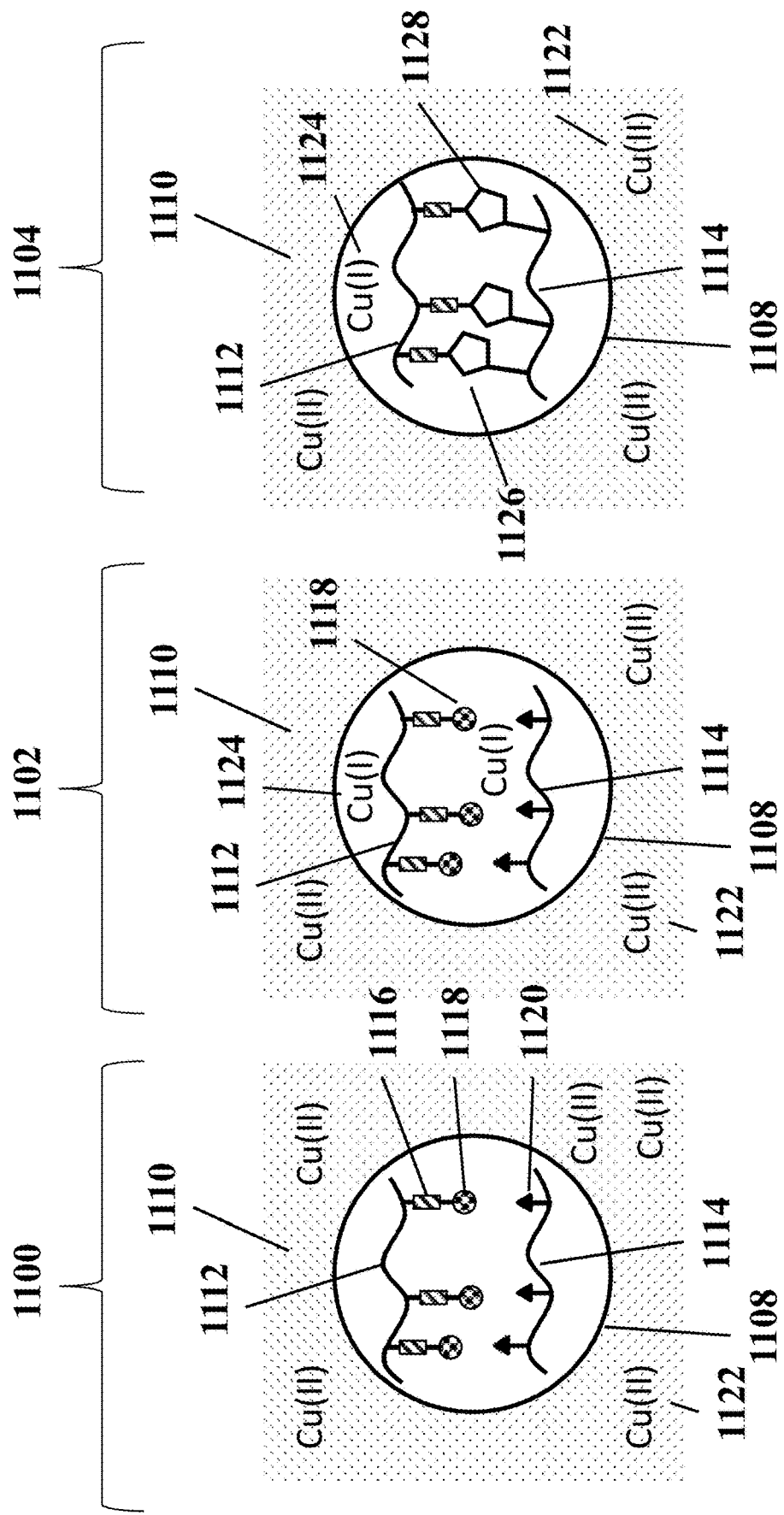
FIG. 11 illustrates an exemplary scheme for cell bead generation or functionalization using crosslinks.

For example, as shown in FIG. 11, emulsion systems 1100, 1102, and 1104 represent different stages through which polymer molecules or gel precursors are crosslinked to form a cell bead matrix or hydrogel. Emulsion system 1100 can comprise a discrete droplet 1108 (comprising an aqueous phase) immersed in an oil phase 1110. Within the discrete droplet 1108, two polymer molecules 1112 and 1114 and an analyte carrier (e.g., a single analyte carrier, such as a single cell—not shown) can be partitioned together. In some instances, a functionalized nucleic acid molecule (not shown, see e.g., 908, 909, and/or 910) is also partitioned with the polymer molecules or gel precursors and the analyte carrier. In some embodiments, the nucleic acid molecule further comprises a functional group (e.g., a click chemistry moiety such as 1118 or 1120) to facilitate attachment to the cell bead matrix. Polymer molecule 1112 can comprise a first crosslink precursor comprising a first click chemistry moiety 1118 and optionally a labile bond 1116 (e.g., a chemically, thermally, enzymatically, or photo-labile bond). Polymer molecule 1114 can comprise a second click chemistry moiety 1120. In the oil phase 1111, there can be other reagents, such as reagent 1122 (shown as a copper (II) reagent), which may be utilized to facilitate the click chemistry reaction between the first click chemistry moiety 1118 and the second click chemistry moiety 1120, either by itself or by a derivative thereof. Because the reagent 1122 remains outside of the discrete droplet 1108, generally no click chemistry reaction happens within the discrete droplet 1108 in the absence of the reagent 1122.

In emulsion system 1102, some of the reagent 1122 can penetrate the discrete droplet 1108, via, e.g., physical or chemical processes. In some instances, reagent 1122 becomes or is otherwise processed to become reagent 1124 (shown as a copper (I) reagent) in the discrete droplet 1108. In some instances, conversion into reagent 1124 requires additional reagents (not shown, e.g., a reducing agent such as sodium ascorbate). In these embodiments, reagent 1124 can be the reagent required to initiate the click chemistry reaction between the first click chemistry moiety 1118 and the second click chemistry moiety 1120. Once in the proximity of both the first click chemistry moiety 1118 and the second click chemistry moiety 1120, the reagent 1124 can initiate a click chemistry reaction, such as a Cu(I)—Catalyzed Azide-Alkyne Cycloaddition (CuAAC), see emulsion system 1104. In embodiments where the functionalized nucleic acid molecules comprise a click-chemistry moiety, the reagent can also catalyze the attachment of nucleic acid molecules to the cell bead matrix.

As shown in the emulsion system 1104 of FIG. 11, in the presence of the reagent 1124, a crosslink 1126 is formed linking the two polymer molecules 1112 and 1114 together, via the newly formed moiety 1128 because of the click chemistry reaction between the first click chemistry moiety 1118 and the second click chemistry moiety 1120. A hydrogel comprising the crosslinked polymer molecules 1112 and 1114 can thus be formed, thereby generating the cell bead. Reagents 1122 and/or 1124 can be removed from the newly formed hydrogel if desired. In some instances, the cell bead matrix comprises a labile bond 1116 (e.g., a disulfide bond) configured to release the crosslinks 1126 and/or degrade the hydrogel upon application of a stimulus (e.g., a chemical, thermal, or photo-stimulus). In some instances, the nucleic acid molecules are attached to the hydrogel via a labile bond 1116 configured to release the nucleic acid molecules from the cell bead matrix.

In some embodiments, the nucleic acid molecule(s) described herein are attached, entrapped, or otherwise incorporated into the cell bead matrix during cell bead generation (see, e.g., FIG. 10 and FIG. 11). In other embodiments, the nucleic acid molecule(s) described herein are attached, entrapped, or otherwise incorporated into the cell bead matrix subsequent to cell bead generation. For example, in some instances, a cell bead can be generated as described elsewhere herein and a nucleic acid molecule can be attached to the cell bead matrix by a chemical reaction, e.g., between a functional group of the nucleic acid molecule(s) and a functional group in the cell bead matrix.

Figure 12A:
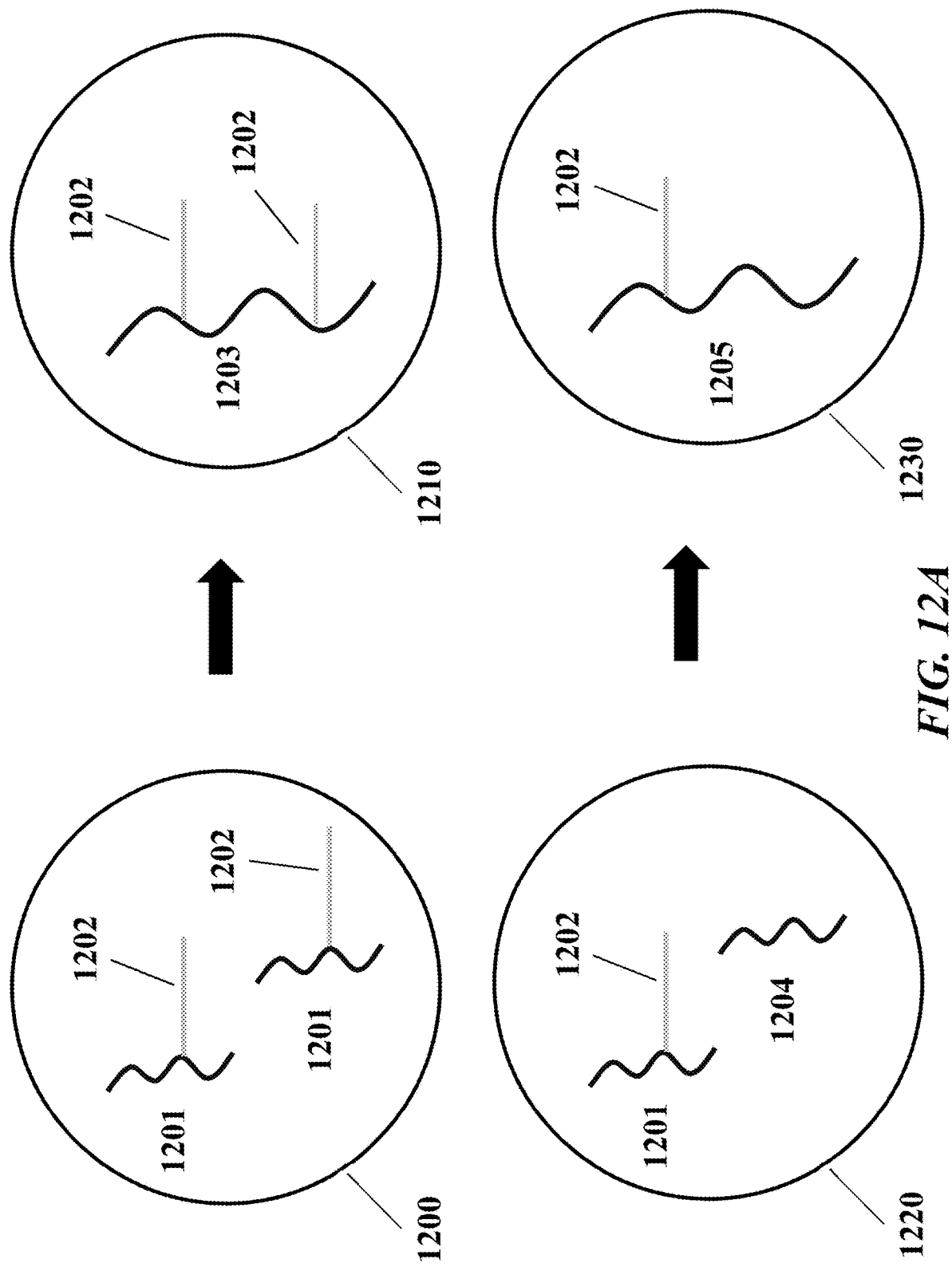
FIGS. 12A-B illustrate exemplary scheme for polymerization or crosslinking of polymer or gel precursors to generate cell beads comprising attached nucleic acid molecules.
Figure 12B:
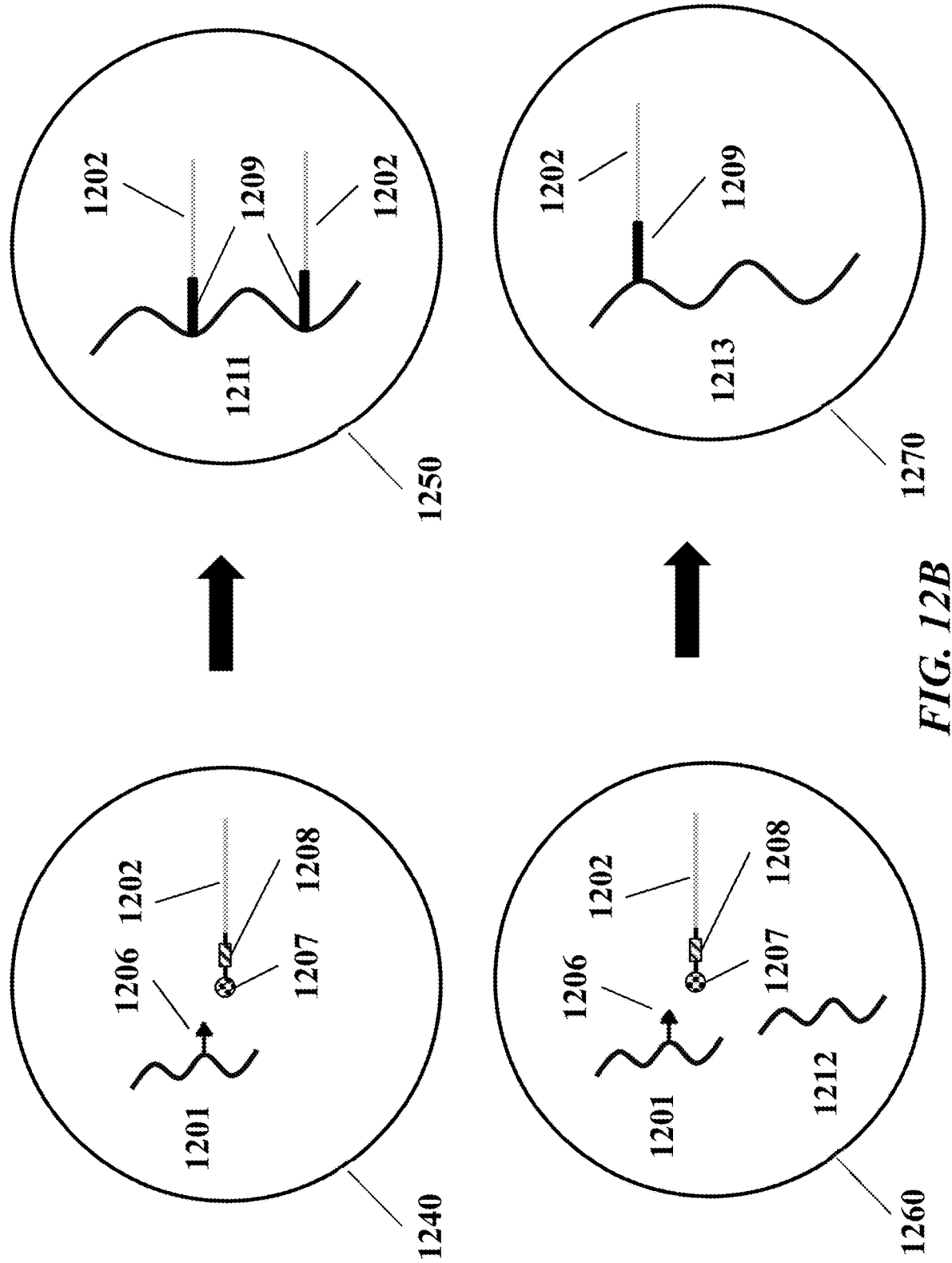

FIGS. 12A-B illustrates an example of generating cell beads comprising functionalized molecule(s) attached to a polymer matrix. For instance, as shown in FIG. 12A, a partition 1200 comprising gel or polymer precursors 1201 attached to a nucleic acid molecule(s) 1202 (e.g., a nucleic acid molecule comprising functional sequences such as 908, 909, and/or 910) can be subjected to conditions sufficient to polymerize, gel, or crosslink the precursors 1201, thereby generating a cell bead 1210 comprising nucleic acid molecule(s) 1202 attached to the polymer matrix 1203. In some instances, a partition 1220 comprising a first polymer or gel precursor 1201 attached to nucleic acid molecule(s) 1202 and a second polymer or gel precursor 1204 can be subjected to conditions sufficient to polymerize, gel, or crosslink precursors 1201 and 1204, thereby generating a cell bead 1230 comprising nucleic acid molecule(s) 1202 attached to a polymer 1205 of polymer or gel precursors 1201 and 1204. In some instances, polymer or gel precursor 1201 is a first type of polymer, polymer or gel precursor 1204 is a second type of polymer, and polymer 1205 is a copolymer of precursors 1201 and 1204. In other instances, polymer or gel precursor 1201 is a first type of polymer comprising a nucleic acid molecule(s) 1202 and polymer or gel precursor 1204 is the same type of polymer as 1201 but lacks nucleic acid molecule 1202.

In other embodiments, as shown in FIG. 12B, a partition 1240 is provided comprising gel or polymer precursors 1201 comprising a first crosslink precursor 1206 (e.g., a first click chemistry moiety) and a nucleic acid molecule(s) 1202 (e.g., a nucleic acid molecule comprising functional sequences such as 908, 909, and/or 910) comprising a second crosslink precursor 1207 (e.g., a second click chemistry moiety), wherein the first crosslink precursor 1206 and the second crosslink precursor 1207 are configured to form a crosslink 1209 thereby linking the nucleic acid molecule(s) 1202 with the polymer or gel precursor 1201 or with a polymerized gelled, or otherwise crosslinked matrix of 1201 (e.g., 1211).

In some instances, a partition 1260 is provided comprising (i) a first polymer or gel precursor 1201 comprising a first crosslink precursor 1206 (e.g., a first click chemistry moiety), (ii) a second polymer or gel precursor 1204, and (iii) a nucleic acid molecule 1202 comprising a second crosslink precursor 1207 (e.g., a second click chemistry moiety), wherein the first crosslink precursor 1206 and the second crosslink precursor 1207 are configured to form a crosslink 1209 thereby linking the nucleic acid molecule 1202 with the polymer or gel precursor 1201 or with a polymerized, gelled, or otherwise crosslinked matrix of 1201 and 1212 (e.g., 1213). In some instances, a partition 1260 comprising the first polymer or gel precursor 1201 attached to nucleic acid molecule 1202 and the second polymer or gel precursor 1212 are subjected to conditions sufficient to polymerize, gel, or crosslink precursors 1201 and 1212, thereby generating a cell bead 1270 comprising nucleic acid molecule(s) 1202 attached to a polymer or gel 1213 of polymer or gel precursors 1201 and 1212. In some instances, polymer or gel precursor 1201 is a first type of polymer, polymer or gel precursor 1212 is a second type of polymer, and polymer 1213 is a copolymer of precursors 1201 and 1212. In other instances, polymer or gel precursor 1201 is a first type of polymer comprising a nucleic acid molecule 1202 and polymer or gel precursor 1212 is the same type of polymer as 1201 but lacks the nucleic acid molecule 1202.

In some instances, one or more agents are utilized to catalyze, initiate, or otherwise facilitate the formation of crosslink 1209. In some instances, the partition 1240 is subjected to conditions sufficient to form a crosslink 1209 between crosslink precursors 1206 and 1209 prior to polymerization, gelling, or crosslinking of polymer precursors (e.g., 1201 and/or 1212) to form cell bead 1250 or 1270. In other instances, the partition (e.g., 1240 or 1260) is subjected to conditions sufficient to form a crosslink 1209 between crosslink precursors 1206 and 1209 concurrently with the polymerization, gelling, or crosslinking of the polymer or gel precursors (e.g., 1201 and/or 1212). In some embodiments, the partition (e.g., 1240 or 1260) is subjected to conditions sufficient to polymerize, gel, or otherwise crosslink the polymer or gel precursors (e.g., 1201 and/or 1212) prior to forming a crosslink 1209 between crosslink precursors 1206 and 1209. In some instances, the nucleic acid molecule 1202 comprises a labile bond 1208 configured to release the crosslink 1209 and the nucleic acid molecule 1202 upon application of a stimulus (e.g., a chemical, thermal, or photo-stimulus).

In some instances, a nucleic acid molecule 1202 is attached to the first polymer or gel precursor (e.g., 1201), the second polymer or gel precursors (e.g., 1204 or 1212), or both the first 1201 and the second polymer or gel precursors (e.g., 1204 or 1212). Furthermore, in some embodiments, additional polymers or polymer or gel precursors can be added (e.g., to partition 1200, 1220, 1240, or 1260) to generate a co-polymer or mixed polymer cell bead matrix. Additionally, the concentration of polymers (e.g., 1201, 1204, and/or 1212) in the partition (e.g., 1200, 1220, 1240, or 1260) can be controlled to generate a cell bead comprising a desired concentration of nucleic acid molecules 1202.

Although FIGS. 12A-B have been generally described above in terms of attaching, e.g., nucleic acid molecules to cell beads, these and other suitable methods are equally applicable in generating functionalized polymers (such as polymer 906). For example, a plurality of polymer precursors (e.g., 1201) comprising a nucleic acid molecule (e.g., 1202) can be subjected to conditions sufficient to polymerize, gel, or crosslink the precursors to generate functionalized polymer 906 comprising nucleic acid molecules (e.g., 1202 comprising functional sequences such as 908, 909, and/or 910). Similarly, although FIGS. 12A-B have been generally described above in terms of attaching, e.g., nucleic acid molecules to, e.g., the cell bead 902 or polymer 906, these and other suitable methods are equally applicable in generating cell beads and polymers comprising other functional molecules such as: chemical species (e.g., biotin, small molecule inhibitors of an enzyme, chelating agents (e.g., aminopolycarboxylates, such as EDTA and EGTA)), aptamers, proteins or polypeptides (e.g., streptavidin, protein A, protein G, antibodies or antigen binding fragments thereof, nanobodies, etc.), enzymes (e.g., a nuclease, transposase, polymerase, helicase, reverse transcriptase, ligase, phosphatase, etc.), lipids, carbohydrates, polysaccharides, and/or glycoproteins.

In some cases, the polymers (e.g., cell bead 902 and/or polymer 906) disclosed herein can comprise poly(acrylic acid), poly(vinyl alcohol), poly(vinylpyrrolidone), poly(ethylene glycol), polyacrylamide, some polysaccharides, or any derivatives thereof. These polymers can be non-toxic and they can be used in various pharmaceutical and biomedical applications. Thus, in some instances, they may not require their removal from the reaction system, thereby eliminating the need for a purification step after the formation of hydrogels.

Polymers (e.g., cell bead 902 and/or polymer 906) can comprise polymer molecules of a particular length or range of lengths. Polymer molecules can have a length of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000, 000, 200,000,000, 500,000,000 or 1,000,000,000 backbone atoms or molecules (e.g., carbons). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000 or 1,000,000,000 backbone atoms or molecules (e.g., carbons). Polymer molecules can have a length of at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 monomer units (e.g., vinyl molecules or acrylamide molecules). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000, 000, 500,000,000 or 1,000,000,000 monomer units (e.g., vinyl molecules or acrylamide molecules).

Partitioning Cell Beads

Figure 13:
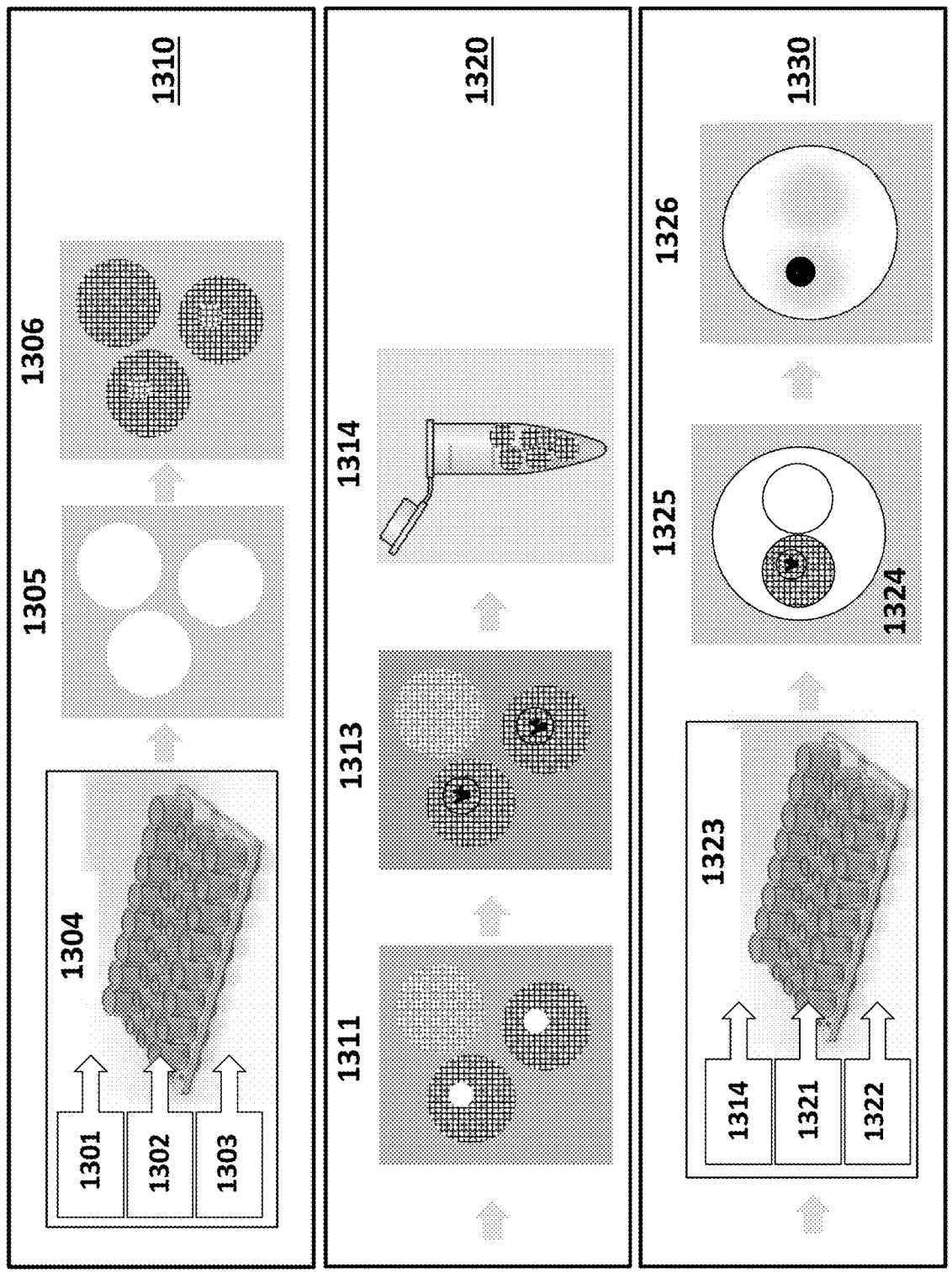
FIG. 13 illustrates an exemplary scheme for cell bead generation and for the generation of partitions comprising cell beads and barcode beads.

Cell beads (optionally comprising nucleic acid molecules comprising functional sequences, e.g., 908, 909, and/or 910) may be partitioned together with nucleic acid barcode molecules (optionally attached to a bead, e.g., 905) and the nucleic acid molecules of or derived from the analyte carrier of the cell bead (e.g., mRNA, cDNA, gDNA, etc,) may be barcoded as described elsewhere herein. In some embodiments, cell beads are co-partitioned (e.g., in a well or droplet emulsion) with a polymer (e.g., 906), and barcode carrying beads 905 (e.g., gel beads) and the nucleic acid molecules of or derived from the cell bead 904 are barcoded as described elsewhere herein. An overview of an exemplary method for generating partitions comprising cell beads and nucleic acid barcode molecules is schematically depicted in FIG. 13. The method described in FIG. 13 comprises three phases 1310, 1320, and 1330 with each respective phase comprising: (1) generation of cell beads (1310); (2) cell bead solvent exchange and optional processing (1320); and (3) co-partitioning of cell beads and barcodes for subsequent tagging (e.g., barcoding) of one or more constituents of (or derived from) the cell bead (1330).

With continued reference to FIG. 13, phase 1310 comprises providing an oil 1301, polymeric or gel precursors 1302, and analyte carriers 1303 (e.g., a cell, a fixed cell, a cross-linked cell, a nucleus, a permeabilized nuclei, etc.) to a microfluidic chip (e.g., 1304) for droplet generation. Functionalized nucleic acid molecules, such as those described elsewhere herein, may be further provided to microfluidic chip 1304 for co-partitioning. In some instances, the functionalized nucleic acid molecules (e.g., 908, 909, and/or 910) are provided with or otherwise attached to the polymeric or gel precursors 1302. In other cases, the functionalized nucleic acid molecules are provided with the analyte carriers 1303. In some instances, the microfluidic chip 1304 comprises a plurality of microfluidic channels (see e.g., FIGS. 1-7) connected to a plurality of reservoirs comprising the oil 1301, polymeric or gel precursors 1302, and analyte carriers (e.g., cells) 1303. Microfluidic chip 1304 may also comprise one or more additional channels and/or reservoirs comprising one or more additional reagents (such as the functional nucleic acid molecules described herein). Polymeric or gel precursors 1302 and analyte carriers 1303 (and in some cases, functional nucleic acid molecules) are flowed (e.g., via the action of an applied force, such as negative pressure via a vacuum or positive pressure via a pump) from their reservoirs through the plurality of microfluidic channels to a first channel junction and combine to form an aqueous stream. This aqueous stream is then flowed to a second channel junction, in which oil 1301 is provided. The aqueous stream provided from the first channel junction is immiscible with the oil 1301 resulting in the generation of a suspension of aqueous droplets 1305 in the oil, which then flow to a reservoir for collection. Flow can be controlled within the microfluidic chip 1304 via any suitable method, including the use of one or more flow regulators in a channel or various channels, dimensioning of microfluidic channels, etc., as described elsewhere herein. As shown in FIG. 13, the product comprises droplets 1305 comprising an analyte carrier 1303, the polymeric or gel precursors 1302, and in some cases, nucleic acid molecules comprising functional sequences (such as 908, 909, and/or 910). In some cases, at least some of the droplets of droplets 1305 comprise a single analyte carrier (e.g., a single cell or single nucleus).

In some embodiments, the droplets 1305 are subjected to conditions sufficient to lyse the analyte carriers (e.g., cells or nuclei) comprised therein, releasing cellular macromolecular constituents into the droplets 1305. The macromolecular constituents (e.g., nucleic acids, proteins, etc.) may additionally be subjected to one or more reactions for processing as described elsewhere herein. In other embodiments, the droplets 1305 are subjected to conditions sufficient to permeabilize the cells (or nuclei) thereby facilitating access to one or more macromolecular constituents of the cell (or nucleus) for further processing. In still other cases, the analyte carriers present in the droplets 1305 are not lysed or permeabilized.

Continuing with FIG. 13, the droplets 1305 comprising analyte carriers are then subjected to conditions suitable to polymerize or gel the polymeric or gel precursors 1302 in the droplets 1305, to generate cell beads 1306. As the resulting cell beads 1306 are suspended in oil, in some embodiments, phase 1320 is initiated which comprises a solvent exchange configured to resuspend the cell beads 1306 in an aqueous phase 1311.

In some embodiments, the resuspended aqueous cell beads 1311 are optionally processed to, e.g., prepare the cell beads for analysis of one or more cellular components. For example, cell beads 1311 can be subjected conditions suitable to lyse or permeabilize analyte carriers (e.g., cells or nuclei) in the cell beads 1313, thereby releasing or otherwise allowing access to one or more cellular constituents (e.g., nucleic acids, such as mRNA and gDNA, proteins, etc.). Separately or contemporaneously from cell lysis, cell beads (e.g., 1311 or 1313) are also subjected to conditions sufficient to denature nucleic acids derived from the cells (e.g., gDNA) associated with the cell beads (e.g., using NaOH). The polymeric matrix of the cell beads (e.g., 1311 or 1313) may effectively hinder or prohibit diffusion of larger molecules, such as nucleic acids and/or proteins, from the cell beads, but may be sufficiently porous to facilitate diffusion of denaturation or other agents into the cell bead matrix to contact nucleic acids and other cellular components within the cell beads. In some cases, the cell beads (1311 or 1313) can be subjected to conditions suitable for performing one or more reactions on nucleic acids or other analytes derived from the cells associated with the cell beads (1311 or 1313). For example, antibodies or a nuclease (e.g., 1603, 1703 as described elsewhere herein) may be washed into and/or out of the resuspended cell beads (1311 or 1313). Additionally, in embodiments where functional nucleic acid molecules are attached or otherwise incorporated into the cell beads subsequent to cell bead generation, functional nucleic acid molecules can be provided and one or more reactions performed on the cell bead (1311 or 1313) to attach or otherwise incorporate the functional nucleic acid molecules into the cell beads (e.g., through functional groups on the functional nucleic acid molecule(s), cell bead matrix, or both). After optional processing, the cell beads comprising cellular constituents can be collected 1314 and stored prior to initiation of phase 1330.

Continuing with FIG. 13, after phase 1320, cell beads 1314 can be analyzed by, e.g., partitioning cell beads and nucleic acid barcode molecules into partitions (e.g., droplets, microwells) for analysis of cellular components (e.g., nucleic acid molecules). For example, in phase 1330, partitions (e.g., droplets) comprising cell beads 1314 and beads (e.g., a gel bead) comprising nucleic acid barcode molecules 1322 ("barcode beads") are generated such that at least some droplets comprise a cell bead and a barcode bead (e.g., a single cell bead and a single barcode bead). In some instances, the partition further comprises a functionalized polymer (e.g., 906). For example, in some embodiments, an oil 1321, the cell beads 1314, barcode beads 1322 each comprising a barcode sequence (e.g., each bead comprising a unique barcode sequence), and a functionalized polymer (e.g., 906) are provided to a microfluidic chip 1323. Exemplary microfluidic chip architecture is shown in e.g., FIGS. 1-7, but any suitable microfluidic chip or microwell array can also be utilized with the compositions, methods, and systems disclosed herein. The microfluidic chip 1323 comprises a plurality of reservoirs comprising the oil 1321, cell beads 1314, barcode beads 1322 (e.g., gel beads), and the high molecular weight functionalized polymer. The chip can also include additional reservoirs that may be used to supply additional reagents (e.g., reagents for nucleic acid amplification, reagents that can degrade or dissolve cell beads and/or gel beads, reagents that degrade linkages between barcode beads/cell beads/polymers, reagents for cell lysis, etc.). Cell beads 1314 and barcode beads 1322 are flowed (e.g., via the action of an applied force, such as negative pressure via a vacuum or positive pressure via a pump) from their reservoirs to, e.g., a first channel junction and form an aqueous mixture.

Alternatively, cell beads, barcode beads (e.g., gel beads), and/or polymers can be mixed before introduction into the microfluidic chip. In this case, a single reservoir of the microfluidic chip (e.g., 1323) comprises a mixture of cell beads, barcode beads (e.g., gel beads), and/or polymers. The ratio of cell beads to barcode beads in the mixture can be varied to alter the number of droplets generated that comprise a single cell bead and a single barcode bead. The mixture of cell beads and barcode beads may be flowed (e.g., via the action of an applied force, such as negative pressure via a vacuum or positive pressure via a pump) from the reservoir to a first channel junction, in some cases together with materials from additional reservoirs.

In some embodiments, the aqueous mixture comprising cell beads 1314, barcode beads 1322, and in some cases additional reagents is then flowed to a second channel junction, to which oil 1321 is provided. The aqueous mixture provided from the first channel junction is immiscible with the oil 1321 resulting in the generation of a suspension of aqueous droplets 1325 in the oil which then flow to a reservoir for collection. Flow can be controlled within the microfluidic chip 1323 via any suitable strategy, including the use of one or more flow regulators in a channel or that connect channels, use of various channels, dimensioning of channels, etc. In some cases, at least some droplets of droplets 1325 comprise a single cell bead and a single barcode bead (e.g., a single gel bead).

Where reagents that degrade or dissolve the cell beads 1314, barcode beads 1322 (e.g., gel beads) and/or linkages between barcodes and barcode beads 1322 (or nucleic acid molecules attached to a functionalized polymer) are present in droplets, these reagents can release the nucleic acids trapped in the cell beads 1313, release the barcodes from the barcode beads 1322, and/or release functionalized acid molecules from the cell bead matrix or polymer. The nucleic acid barcode molecules can interact with the released cellular components (e.g., cellular nucleic acids) and generate barcoded nucleic acid molecules for nucleic acid sequencing as described elsewhere herein. In embodiments where the barcode bead (e.g., gel bead) is degraded or nucleic acid barcode molecules are releasably attached to the barcode bead (e.g., gel bead), the barcoded cellular components (e.g., barcoded cDNA or gDNA fragments) are not attached to the bead. Where a given droplet comprises a cell bead (e.g., a single cell bead) and a barcode bead (e.g., a single barcode bead) comprising nucleic acid barcode molecules comprising a common barcode sequence, the barcoded cellular components (or derivatives thereof) can be associated with the analyte carrier (e.g., a cell or other biological sample, such as a bacterium or virus) of the given cell bead via the common barcode sequence.

Cellular Processing

In some aspects, disclosed herein are methods for processing and analysis of nucleic acids from one or more cells. The described methods may be used in conjunction with one or more compositions disclosed herein. For example, partitions, cell beads, barcode beads, and/or polymers may be used in methods of nucleic acid analysis.

First, a partition may be generated comprising a cell bead comprising a nucleic acid, a nucleic acid barcode molecule, and a polymer. Next, the nucleic acid and the nucleic acid barcode molecule may be used to perform one or more reactions in the partition. A partition may be a droplet. A partition may be a well. A reaction may be performed outside the cell bead. A reaction may comprise nucleic acid extension. A reaction may comprise nucleic acid amplification (e.g., PCR, linear amplification. etc.). A reaction may comprise generating a barcoded nucleic acid from the nucleic acid and the nucleic acid barcode.

A cell bead may comprise a nucleus. A cell bead may comprise a permeabilized nucleus. A cell bead may comprise a nucleic acid (e.g. DNA, RNA, etc) derived from a cell and/or a nucleus. A nucleic acid barcode molecule may be attached to a barcoded bead. A nucleic acid barcode molecule may be releasably attached to a barcoded bead.

A polymer may be incapable of diffusing into a cell bead. A polymer (e.g., polymer 906) may be a functionalized polymer (e.g., may comprise one or more additional reagents). A polymer may be a linear polymer. A polymer may be a branched polymer. A polymer may be attached to a reagent. A reagent may be, for example, an enzyme, a nucleic acid, a chemical compound, or a protein. A polymer may be functionalized with a chemical compound. A chemical compound may be an inhibitor of an enzyme. A chemical compound may be, for example, deoxythymidine 3',5'-bisphosphate or ethylene glycol-bis(β-aminoethyl ether)-N,N,N',N'-tetraacetic acid (EGTA). A polymer may be functionalized with a charged species. A polymer may comprise an oligonucleotide comprising a capture sequence. A capture sequence may be a poly-T sequence, a random sequence, or an rRNA capture sequence.

A partition (e.g., droplet) may comprise an enzyme. An enzyme may be, for example, a nuclease, transposase, polymerase, helicase, reverse transcriptase, ligase, or phosphatase. In some cases, an enzyme is a nuclease. A nuclease may be a micrococcal nuclease (MNase) or a DNase. An enzyme may be an engineered enzyme. An engineered enzyme may be an engineered nuclease. An engineered enzyme may comprise a ligand attached thereto. A ligand may be, for example, biotin. An engineered nuclease may be modified with a ligand such that, upon binding of a ligand-binding protein to the ligand, the enzyme is inactivated.

An enzyme may be attached to a binding moiety. A binding moiety may be an antibody or fragment thereof. An enzyme may be attached to a binding moiety directly (e.g., covalently). An enzyme may be attached to a binding moiety indirectly (e.g., non-covalently). A nuclease may be attached to a binding protein (e.g., Protein A, Protein G). An enzyme may be attached to a binding moiety via a binding protein. A binding moiety may be capable of binding to a nucleic acid binding protein (e.g., transcription factor, histone, etc.). A partition may comprise one or more cations for activating an enzyme. Examples of cations include magnesium ($Mg^{2+}$) and calcium ($Ca^{2+}$).

Compositions and methods described herein may comprise one or more enzymes. Enzymes may be useful in, for example, performing one or more reactions with nucleic acid(s) in or derived from a cell. An enzyme for use in the disclosed methods and compositions may be any suitable enzyme capable of modifying or processing a nucleic acid. An enzyme may be a transposase. An enzyme may be a polymerase. An enzyme may be a helicase. An enzyme may be a reverse transcriptase. An enzyme may be a ligase. An enzyme may be a phosphatase. An enzyme may be a nuclease. A nuclease may be a DNase. A nuclease may be a micrococcal nuclease (MNase).

Figure 14:
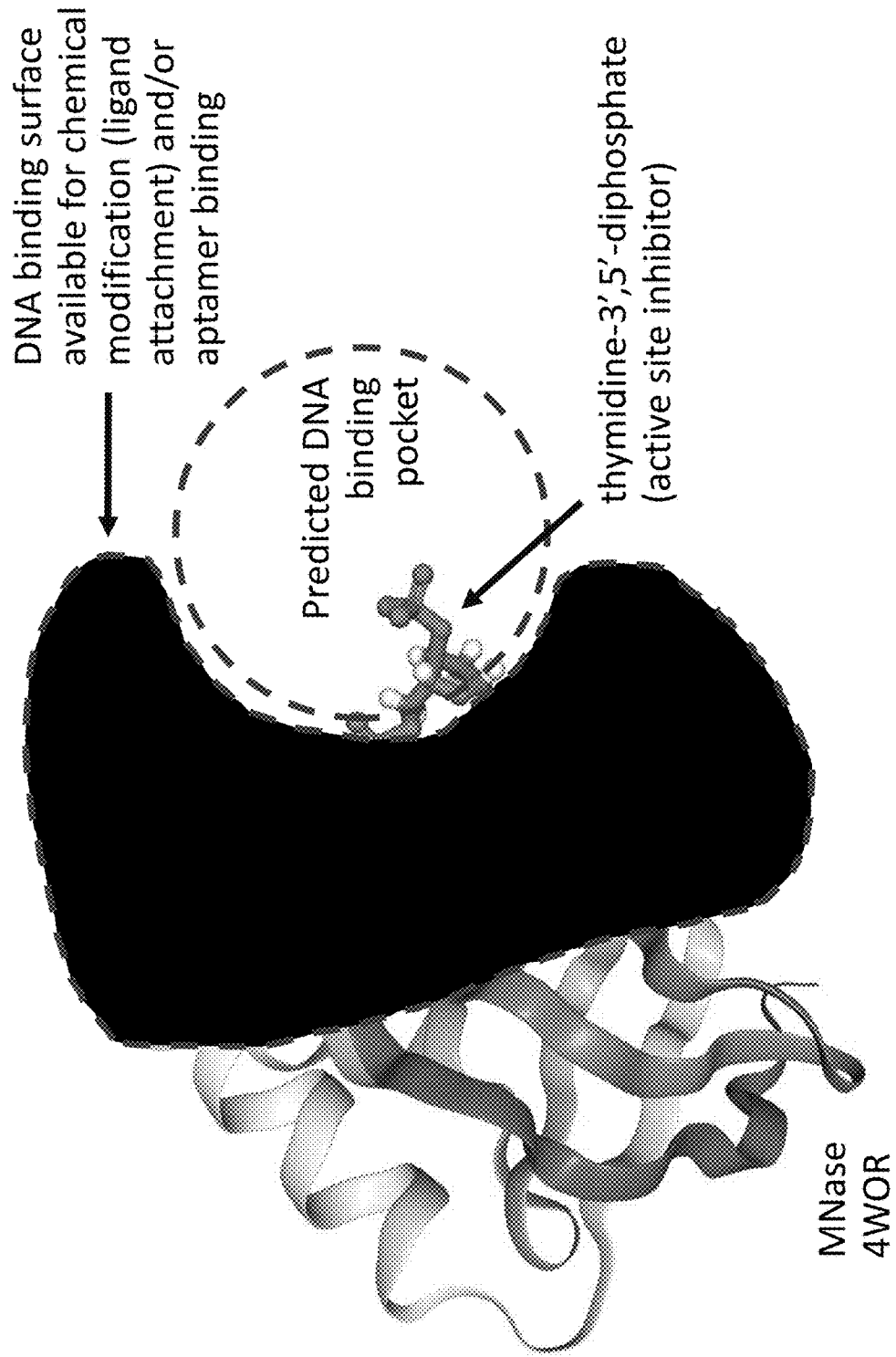
FIG. 14 shows a structure of a micrococcal nuclease (MNase).

An enzyme may be an engineered enzyme. An engineered enzyme may be an enzyme that has been modified, for example, via protein engineering or chemical modification. An enzyme may be modified via the addition of one or more chemical moieties (e.g., ligands, aptamers, etc.), thereby generating an engineered enzyme. An engineered enzyme may be used in the disclosed methods for performing one or more reactions on a nucleic acid. An engineered enzyme may be engineered such that, e.g., the enzyme is active inside a cell or cell bead and inactive/less active outside a cell or cell bead. For example, an enzyme may be engineered to comprise a binding moiety capable of binding to or interacting with a binding partner such that when the binding partner is bound to the binding moiety, the enzyme has reduced enzymatic activity, is functionally inactivated, and/or is otherwise sequestered from additional substrates. For example, an engineered enzyme may comprise a binding moiety such as a ligand, chemical compound, chemical group (e.g., alkyne, azide, etc.), small molecule, carbohydrate, aptamer, and/or polypeptide (such as an epitope tag). For example, in some embodiments, the engineered enzyme comprises a biotin moiety, wherein upon interaction of the biotin with its binding partner (e.g., streptavidin), the engineered enzyme is functionally inactivated or otherwise sequestered from further enzymatic reactions. An engineered enzyme may comprise a binding moiety within, near, or otherwise adjacent to the active site of the enzyme, such that binding of the binding partner thereby inhibits the enzyme (e.g., through steric effects, reversible/irreversible inhibition, substrate competition, etc.). The active site surface of an enzyme may be predicted from protein structure and/or homology and a suitable modification (e.g., a binding moiety) may be selected to generate the engineered enzyme. For example, FIG. 14 shows a 3-D ribbon structure of a MNase, highlighting the active site (predicted DNA binding pocket), $Ca^{2+}$ ion (MNase is strictly dependent on calcium for activity), and the DNA binding surface available for chemical modification (e.g., binding moiety attachment) and/or antibody or aptamer binding.

For example, FIGS. 15A-15C illustrate an exemplary engineered nuclease comprising a binding moiety. FIG. 15A shows an enzyme 1520, capable of fragmenting nucleic acid 1510 into fragments 1511 within the active site of the enzyme. FIG. 15B shows an engineered nuclease 1530 comprising a binding moiety 1531 (e.g., a biotin molecule). In the absence of a binding moiety binding partner 1540 (e.g., streptavidin), engineered nuclease 1530 is capable of fragmenting nucleic acid 1510 into fragments 1511. FIG. 15C shows engineered nuclease 1530 comprising binding moiety 1531 (e.g., a biotin molecule) bound to binding moiety binding partner 1540 (e.g., streptavidin). With binding moiety binding partner 1540 bound to binding moiety 1531, the enzymatic activity of engineered nuclease 1530 is reduced and/or inhibited, thereby reducing/inhibiting fragmentation of nucleic acid 1510.

An engineered enzyme (e.g., 1530) may be attached to a binding moiety (e.g., 1531). An engineered enzyme may be directly or indirectly attached to a binding moiety. An engineered enzyme may be directly attached to a binding moiety via a linker. An engineered enzyme may be indirectly attached to a binding moiety via a binding protein. A binding moiety may be an antibody or fragment thereof (e.g., a nanobody, an scFv, etc.). An engineered enzyme may be attached to a binding protein capable of binding a binding moiety. For example, an enzyme may be attached to Protein A or Protein G. A binding protein may bind to a binding moiety, thereby indirectly attaching an enzyme to the binding moiety. A binding moiety may be capable of binding to a nucleic acid binding protein. For example, a binding moiety may be an antibody or antibody fragment capable of binding to a specific nucleic acid binding protein, thereby directing an enzyme to a specific region of a nucleic acid.

Figure 16:
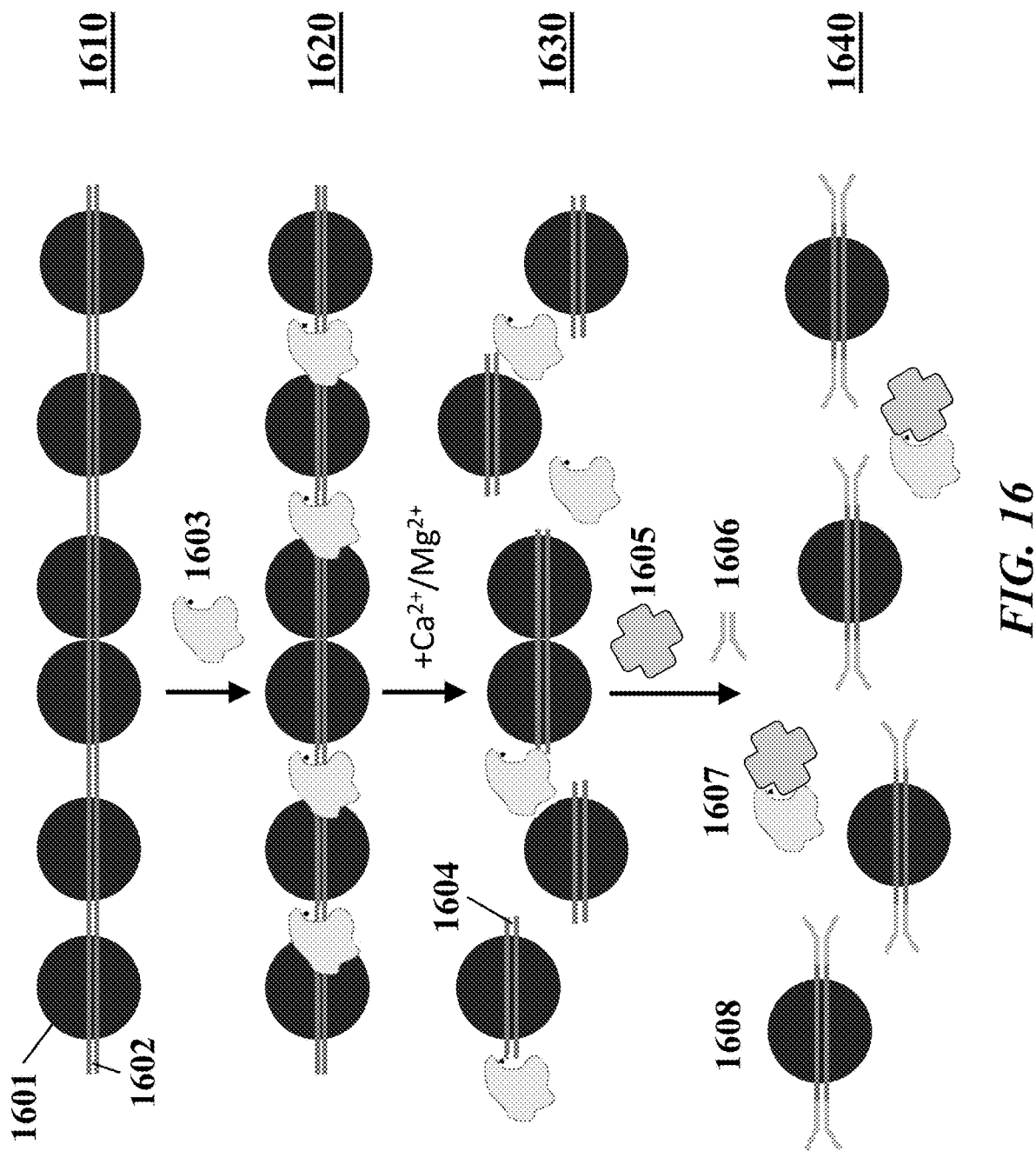
FIG. 16 illustrates an exemplary method for fragmenting and barcoding chromatin fragments, using an engineered nuclease.

FIG. 16 shows an example cellular processing method comprising nucleic acid fragmentation and barcoding. In operation 1610, cellular chromatin comprising nucleosomes 1601 (and/or DNA-binding proteins) and genomic DNA 1602 are provided (e.g., from a cell or nucleus). In operation 1620, engineered nucleases 1603 (e.g., an engineered MNase) are provided, each comprising a binding moiety within/adjacent to the active site. In operation 1630, cations calcium ($Ca^{2+}$) and/or magnesium ($Mg^{2+}$) are added, thereby activating engineered nucleases 1603 and fragmenting DNA 1602 to generate nucleic acid fragments 1604. The cations may be added by, for example, co-partitioning the chromatin, engineered nucleases 1603, and cations into a partition. In operation 1640, binding moiety binding proteins 1605 and barcoded adaptors 1606 (optionally attached to a bead) are provided. As such, in some instances, operations 1610 and 1620 may be performed outside a partition, while operations 1630 and 1640 may be performed inside one or more partitions (e.g., a droplet or well). Binding moiety binding proteins 1605 bind to and inhibit engineered nucleases 1607. Ligases (not shown in FIG. 16) are used to attach barcoded adaptors 1606 to the nucleic acid fragments 1604, thereby generating barcoded nucleic acid fragments 1608. Binding protein bound to engineered nuclease 1607 prevents the engineered nuclease from digesting the barcoded nucleic acid fragments 1608. Binding moiety binding proteins 1605 may be attached to a functionalized polymer (e.g., 906), as described elsewhere herein. Although shown as a Y-adapter in 1606, any suitable nucleic acid barcode molecule, such as those described herein, are contemplated.

Figure 17:
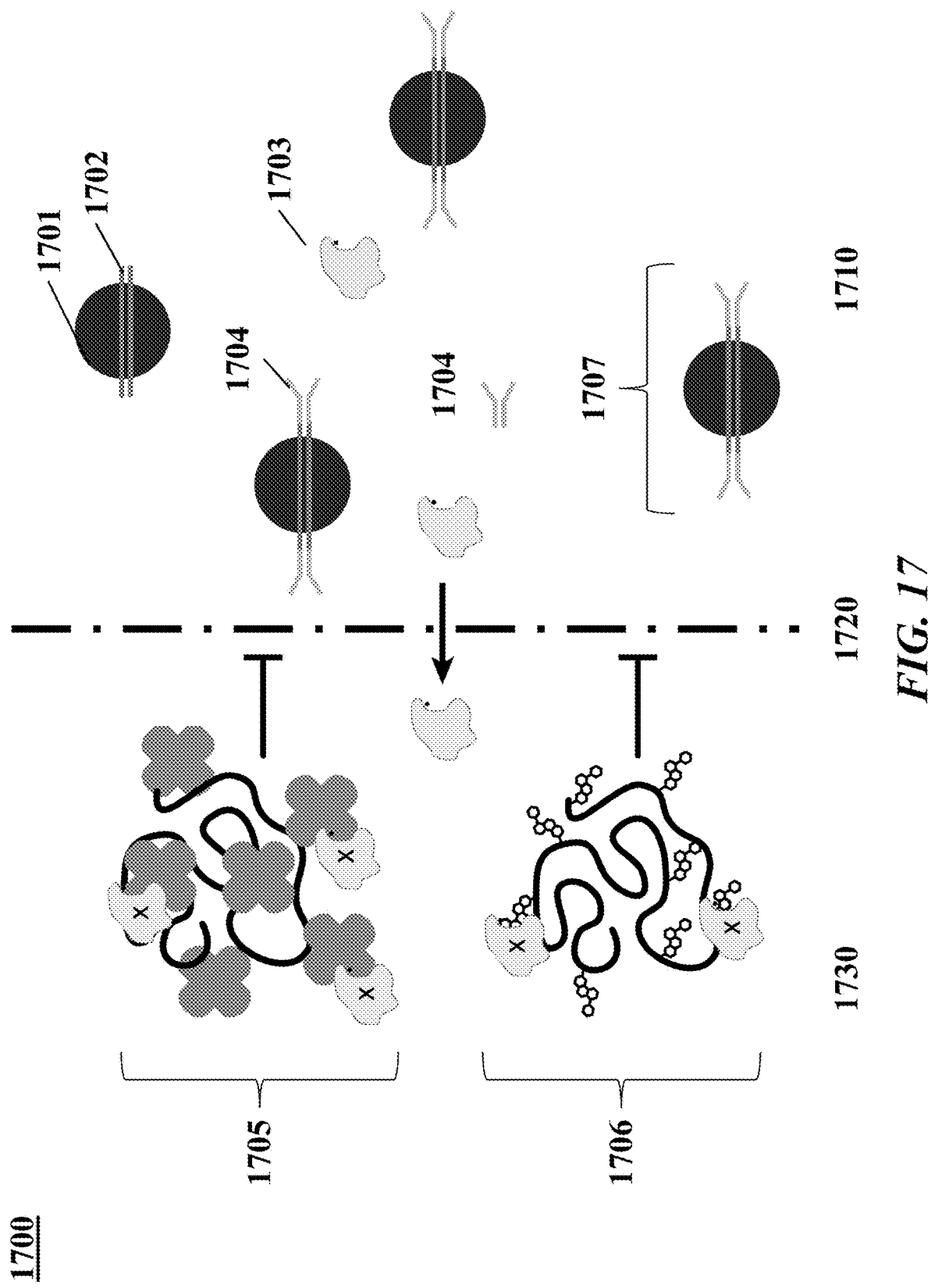
FIG. 17 illustrates an exemplary method for inhibiting a nuclease using a functionalized high molecular weight polymer.

FIG. 17 shows an example of inhibition of an engineered nuclease using a functionalized polymer (e.g., 906). Partition 1700 (e.g., an aqueous droplet in an emulsion or a well of a microwell array) comprises a porous cell bead 1710 with a porosity that allows some molecules (e.g., 1703) to freely diffuse through the cell bead boundary 1720 into the aqueous environment of the partition 1730 while entrapping other molecules (e.g., 1707) within the cell bead matrix 1710. The size of molecules entrapped within the cell bead matrix may be dependent on the characteristics of the cell bead (e.g., polymer makeup, porosity, etc.). Within the cell bead matrix 1710, nucleases 1703 (e.g., MNase or a transposase, such as an adapter-loaded transposase) are capable of fragmenting chromatin to generate nucleic acid fragments 1702 (e.g., attached to nucleosomes 1701 or free nucleic acid molecules representative of areas of accessible chromatin, such as in ATAC-seq). The nuclease 1703 may be an engineered nuclease and comprise a binding moiety (e.g., biotin, polypeptide, aptamer, etc.) as described herein. When engineered nuclease 1703 diffuses through the cell bead boundary 1720 it may attach to a functionalized polymer comprising a binding moiety binding partner 1705 (e.g., streptavidin), thereby inhibiting the enzymatic activity and/or sequestering the enzyme from reactants. In some instances, when nuclease 1703 diffuses through the cell bead boundary 1720, it may attach to a functionalized polymer comprising an inhibitor 1706 (e.g., a small molecule inhibitor), thereby inhibiting the enzymatic activity and/or sequestering the enzyme from reactants. In some embodiments, when nuclease 1703 diffuses through the cell bead boundary 1720, the nuclease 1703 is inactivated and/or sequestered by a functionalized polymer comprising a molecule specific for nuclease 1703 (e.g., an antibody, aptamer, or other binding moiety that when bound to nuclease 1703 occludes the active site from interacting with substrate—see, e.g., FIG. 14). In still other instances, when nuclease 1703 diffuses through the cell bead boundary 1720, the nuclease 1703 is inactivated by a functionalized polymer comprising a small molecule inhibitor (e.g., deoxythimidine 3',5'-bisphosphate, EDTA, EGTA, etc.). Polymer complexes (e.g., 1705 and 1706) are incapable of diffusing into cell bead 1710. A ligase or polymerase (not shown in FIG. 17) can then attach nucleic acid barcode molecules 1704 (which are permeable to cell bead 1710 and may optionally be attached to a bead, e.g., 905) to nucleic acid fragments 1702. Inhibition of the nucleases 1703 by binding to the functionalized polymer (e.g., 1705 and/or 1706) prevents removal of the nucleic acid barcode molecules from the nucleic acid fragments. Although shown as a Y-adapter in 1704, any suitable nucleic acid barcode molecule, such as those described herein, are contemplated.

Figure 18:
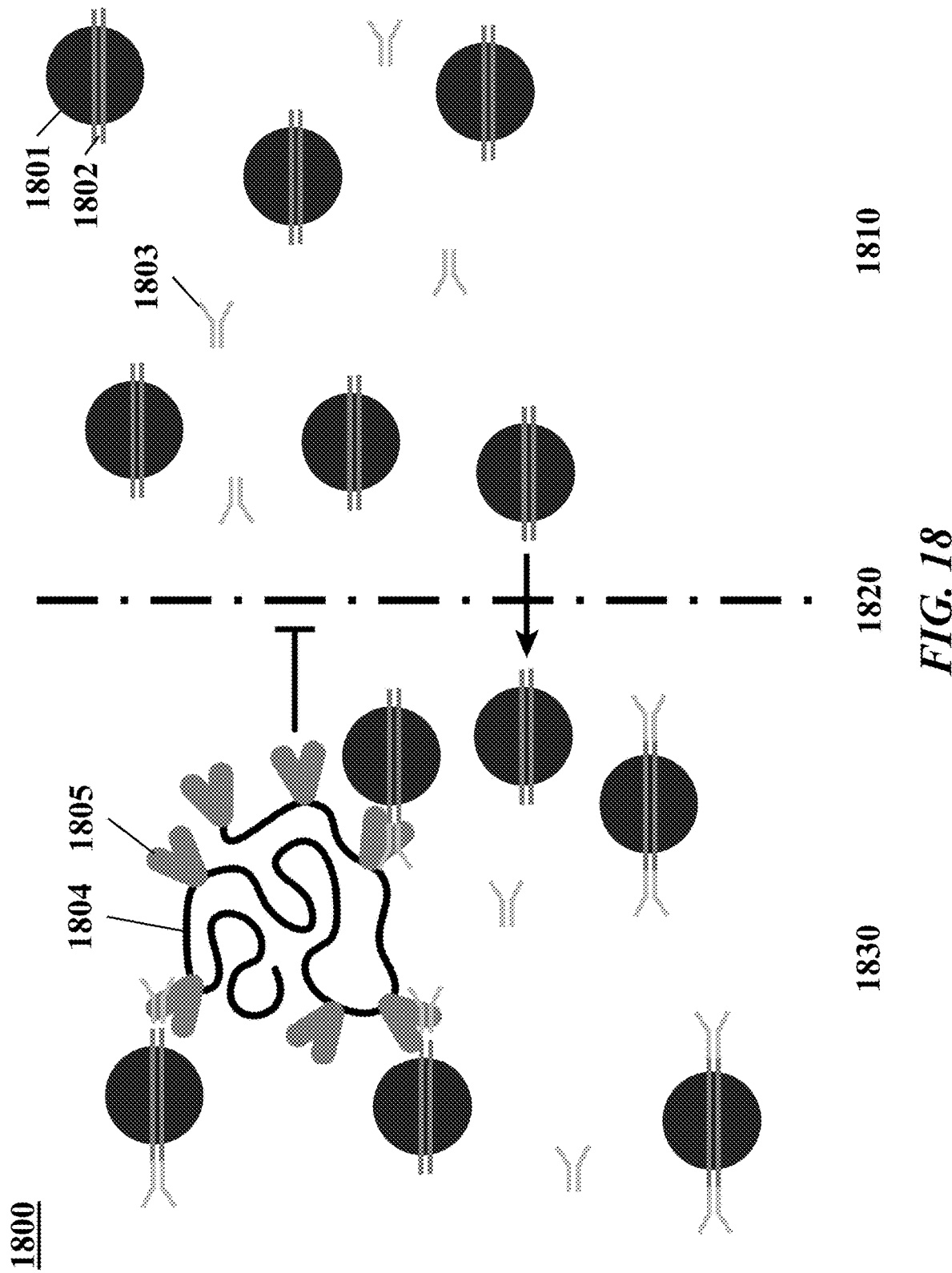
FIG. 18 illustrates an exemplary method for processing a nucleic acid molecule using an enzyme linked to a high molecular weight polymer.

FIG. 18 shows an example of a polymer 1804 functionalized with an enzyme 1805 (e.g., a nuclease, transposase, polymerase, helicase, reverse transcriptase, ligase, phosphatase, or any other suitable enzyme that modifies DNA or RNA) for use in spatially controlling reactions such as nucleic acid barcoding. Partition 1800 (e.g., an aqueous droplet in an emulsion or a well of a microwell array) comprises a porous cell bead 1810 with a cell bead boundary 1820. Within the cell bead 1810, nucleases (e.g., MNase or a transposase, such as an adapter-loaded transposase) are capable of fragmenting chromatin to generate nucleic acid fragments 1802 (e.g., attached to nucleosomes 1801 or free nucleic acid molecules representative of areas of accessible chromatin, such as in ATAC-seq). Partition 1800 also comprises nucleic acid barcode molecules 1803 (which are permeable to cell bead 1810 and may optionally be delivered to partition 1800 on a bead, e.g., 905). Although shown as a Y-adapter in 1803, any suitable nucleic acid barcode molecule, such as those described herein, are contemplated. Outside the cell bead 1810, functionalized polymer 1804 may comprise an enzyme 1405 (e.g., a ligase). Polymer 1804, attached to enzyme 1805, is incapable of diffusing into through the semi-permeable cell bead boundary 1810 into cell bead 1820. Nucleic acid fragments 1802, nucleosomes 1801, and/or nucleic acid barcode molecules 1803 may diffuse out of the porous cell bead 1810 and into the aqueous partition environment 1830. Enzyme 1805 (e.g., a ligase or polymerase) may be used to attach nucleic acid barcode molecules 1803 to the nucleic acid fragments 1802 outside the cell bead 1810.

Figure 19:
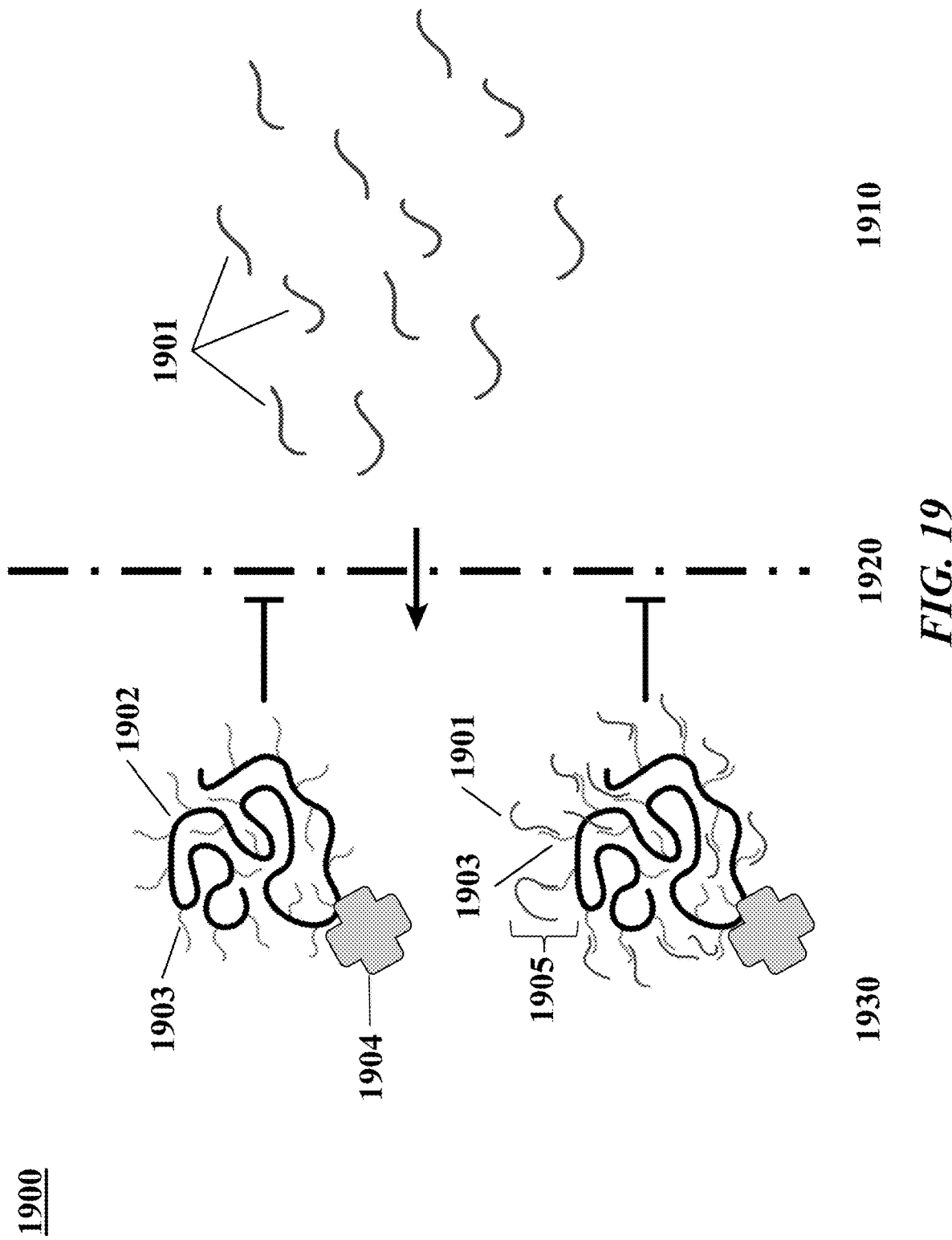
FIG. 19 illustrates an exemplary method for capturing a nucleic acid molecule using a functionalized high molecular weight polymer.

FIG. 19 shows an example of a polymer 1902 functionalized with a nucleic acid molecule 1903 comprising capture sequences configured to capture nucleic acids from a cellular sample. Partition 1900 (e.g., an aqueous droplet in an emulsion or a well of a microwell array) comprises a porous cell bead 1910 with a cell bead boundary 1910. Within the cell bead 1910 are cellular nucleic acid molecules 1901 (e.g., mRNA molecules, rRNA molecules, gDNA fragments, etc.). Nucleic acid molecules 1901 may be released from a cell or nucleus within the cell bead 1910. Outside the cell bead, functionalized polymer 1902 may comprise a nucleic acid molecule 1903 comprising a capture sequences (e.g., targeted capture sequences, rRNA capture sequences, random N-mer sequences, poly-T sequences, etc.) and optionally an affinity handle 1904 (e.g., streptavidin, GST, His-tag, an antibody or portion thereof, etc.) configured to facilitate isolation, removal, purification, etc. of the polymer-bound molecules. Nucleic acid molecule 1903 may further comprise functional sequences such as barcode sequences, UMIs, sequencing adaptors, or any other functional sequence. Nucleic acid molecules 1901 may diffuse out of the porous cell bead 1901 and attach (e.g., hybridize or be ligated) to capture sequences in nucleic acid molecule 1903 to form complexes 1905. Nucleic acid molecules 1901 bound in complexes 1905 may be further processed in partition 1900 or in bulk (e.g., to generate cDNA from mRNA molecules). Complexes 1905 may be purified from partition 1900, for example, by use of affinity handle 1904, thereby isolating nucleic acid molecules (e.g., RNA, cDNA molecules, etc.).

Epigenetic Profiling

In some aspects, disclosed herein are methods for generating a barcoded nucleic acid. A barcoded nucleic acid may be useful in, for example, epigenetic profiling of one or more cells. First a cell bead may be generated comprising a permeabilized nucleus and a nuclease. In some cases, a cell bead may further comprise a particle (e.g., a magnetic particle). Next, a cell bead, nucleic acid barcode molecule, and a polymer may be co-partitioned into a partition. A polymer may be functionalized with an inhibitor of the nuclease. Next, the nuclease may be used to fragment a nucleic acid from the nucleus, thereby generating a nucleic acid fragment. Next, the nucleic acid fragment and the nuclease may be released from the cell bead into the partition. The nuclease may come in contact with the inhibitor attached to the polymer, thereby inhibiting the nuclease. Finally, the nucleic acid fragment and the nucleic acid barcode molecule may be used to generate a barcoded nucleic acid. For example, a ligase enzyme may be used to attach the nucleic acid barcode molecule to the nucleic acid fragment, or a derivative thereof (e.g., a complement thereof, a nucleic acid extension product thereof, etc.).

A nuclease may be attached to a binding moiety. A binding moiety may be an antibody or fragment thereof. A nuclease may be attached to a binding moiety directly (e.g., covalently). A nuclease may be attached to a binding moiety indirectly (e.g., non-covalently). A nuclease may be attached to a binding protein (e.g., Protein A, Protein G). A nuclease may be attached to a binding moiety via a binding protein. A binding protein may localize a nuclease within a cell bead based on the binding properties of the binding protein. In one example, a binding protein is an antibody or fragment thereof with specificity for a nucleic acid binding protein. In this example, a nuclease may be attached to the antibody and therefore localized to the nucleic acid binding protein in a nucleus. A nuclease may be used to fragment a nucleic acid. A localized nuclease may fragment nucleic acid only in a given region. For example, a nuclease may be localized to the region of a histone and used to fragment DNA in the region of the histone, generating DNA fragments corresponding to the region of DNA around the histone.

In some cases, a barcoded nucleic acid may be released from a partition for further processing. A barcoded nucleic acid may be subjected to nucleic acid sequencing, thereby generating sequences corresponding to a nucleic acid from a cell or nucleus. For example, a barcoded nucleic acid may generate sequences from genomic DNA of a nucleus corresponding to a given region. The region may be determined based on localization of a nuclease within a nucleus. Sequences may be analyzed to generate a genetic and/or epigenetic profile of one or more single cells.

Figure 20:
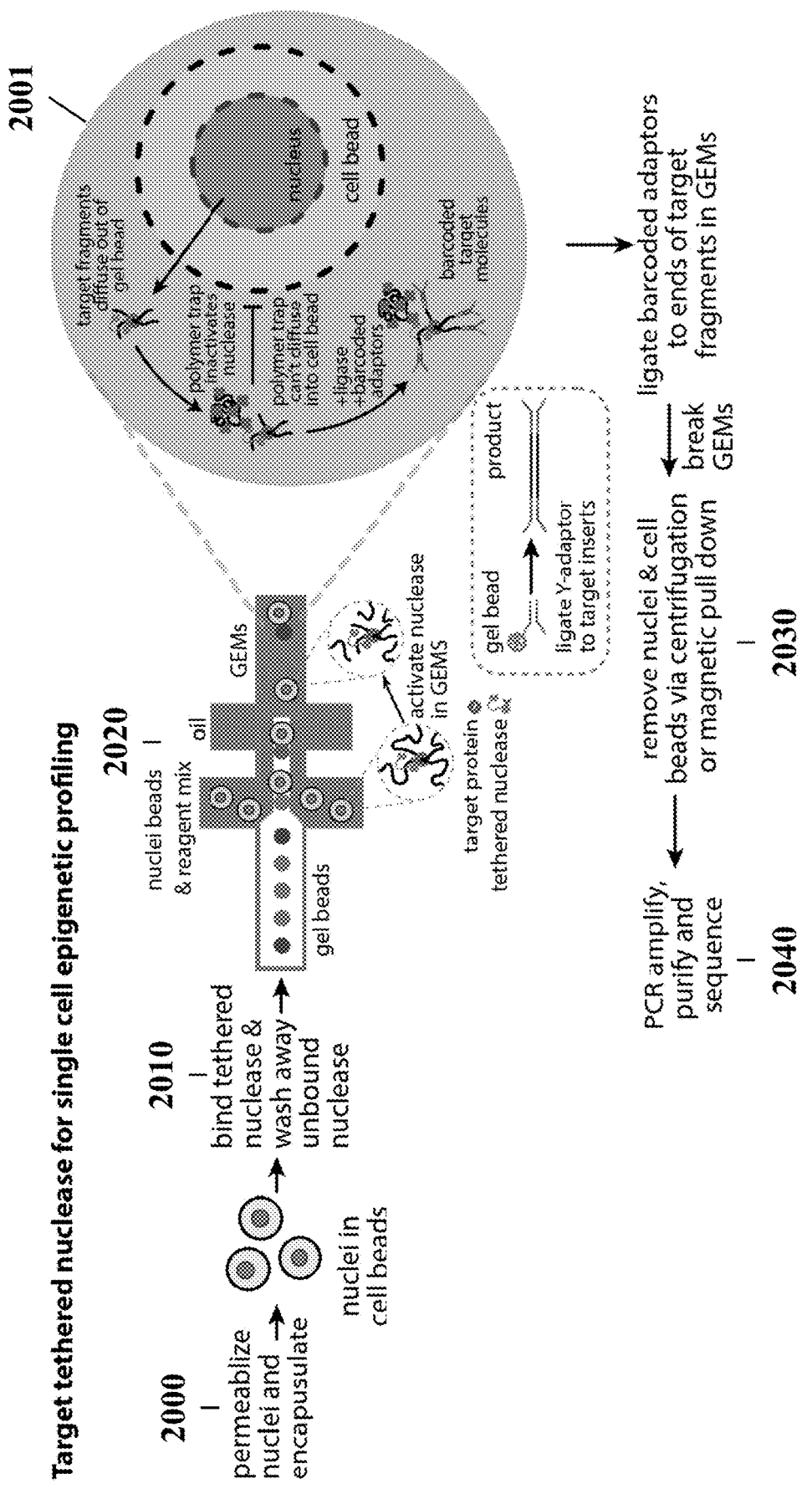
FIG. 20 shows an exemplary method for epigenetic profiling of chromatin from single cells.

FIG. 20 shows an example method for epigenetic profiling of chromatin. In operation 2000, nuclei from a plurality of cells may be obtained and permeabilized. Each nucleus may be captured in a cell bead, as described herein (see, e.g., FIG. 13). In some cases, a cell bead may further comprise a particle, such as a magnetic particle. In operation 2010, cell beads may be placed in an aqueous solution comprising a nuclease (e.g., DNase, MNase, etc.) attached to a binding moiety (e.g., an antibody or fragment thereof). A binding moiety may be capable of binding to a histone or other nucleic acid binding protein, such as a transcription factor. A nuclease may be attached to a binding moiety directly (e.g., via covalent linkage). A nuclease may be attached to a binding moiety indirectly. A nuclease may be attached (e.g., covalently linked) to a binding protein capable of binding to a binding moiety (e.g., protein A, protein G, etc.). The binding moiety attached to the nuclease (the "tethered nuclease") may be brought in contact with the chromatin within the nuclei. The binding moiety may bind to a component of the chromatin (histone, transcription factor, etc.). In some cases, the aqueous solution may not comprise the necessary reagents for nuclease activity (e.g., cations such as $Mg^{2+}$ and $Ca^{2+}$), such that the nuclease is bound to the chromatin in the cell bead in an inactive state. In some cases, any nuclease which is not bound to the chromatin may be removed, e.g., by washing the cell beads.

In operation 2020, cell beads may be partitioned into droplets together with a plurality of barcode beads (e.g., gel beads), such that a given droplet 2001 contains a single cell bead and a single barcoded bead. Additionally, a high molecular weight, functionalized polymer (e.g., 906) may be partitioned into the droplet with the cell bead and barcoded bead. The functionalized polymer may comprise a protein, chemical compound, or other means for inactivating the nuclease. For example, the functionalized polymer may comprise a chemical compound capable of inhibiting the nuclease. The functionalized polymer may comprise a binding moiety binding partner (e.g., streptavidin) capable of binding to a binding partner (e.g., biotin) attached to the nuclease. The functionalized polymer may comprise a chelation agent, such as EGTA or EDTA, capable of chelating one or more cofactors necessary for enzymatic activity of the nuclease.

The functionalized polymer may comprise nucleic acid molecules comprising one or more functional sequences (e.g., the functional sequences 908, 909, and/or 910 described elsewhere herein) configured to facilitate one or more interactions or reactions with a component (e.g., a cellular nucleic acid) from a cell bead. The functionalized polymer may also comprise nucleic acid molecules comprising other functional sequences, such as barcode sequences, a unique molecular index (UMI) sequence, a sequencing primer sequence (or a partial sequencing primer sequence, such as a partial R1 and/or R2 sequence), and/or one or more adaptor sequences, such as a sequence configured to attach to the flow cell of a sequencer (e.g., P5, P7), etc. Droplet 2001 may also comprise the necessary reagents for nuclease activity (e.g., cations such as $Mg^{2+}$ and $Ca^{2+}$), thereby activating the nuclease. The nuclease may fragment nucleic acid within the chromatin of the nucleus, thereby releasing nucleic acid fragments and the nuclease from the cell bead into the surrounding droplet. The functionalized polymer may inactivate the nuclease, preventing further DNA fragmentation.

As depicted in FIG. 20, the droplet may also comprise a ligase enzyme and nucleic acid barcode molecules attached to the barcode bead. The ligase enzyme may be used to attach the nucleic acid barcode molecules to the nucleic acid fragments, thereby barcoding the nucleic acid molecules from the nucleus. In operation 2030, barcoded molecules may then be released from the droplets, and cell beads removed, for example, via centrifugation or magnetic pull down. In operation 2040, Barcoded nucleic acid molecules may be subjected to amplification (e.g., PCR amplification), purification, and/or nucleic acid sequencing. Nucleic acid sequencing results may be used to identify an epigenetic profile of each single cell from the original plurality of cells.

Systems and Methods for Sample Compartmentalization

In an aspect, the systems and methods described herein provide for the compartmentalization, depositing, or partitioning of one or more particles (e.g., analyte carriers, macromolecular constituents of analyte carriers, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles (or analyte carriers) and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be an analyte carrier and/or one or more of its macromolecular constituents encased inside of a gel or polymer matrix, such as via polymerization of a droplet containing the analyte carrier and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual analyte carriers, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of analyte carriers per partition, number of beads per partition, etc.). For example, partition occupancy can be controlled by providing the aqueous stream at a certain concentration and/or flow rate of particles. To generate single analyte carrier partitions, the relative flow rates of the immiscible fluids can be selected such that, on average, the partitions may contain less than one analyte carrier per partition in order to ensure that those partitions that are occupied are primarily singly occupied. In some cases, partitions among a plurality of partitions may contain at most one analyte carrier (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or analyte carriers, e.g., cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles or analyte carriers, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114 (or analyte carriers), and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (or analyte carriers) (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
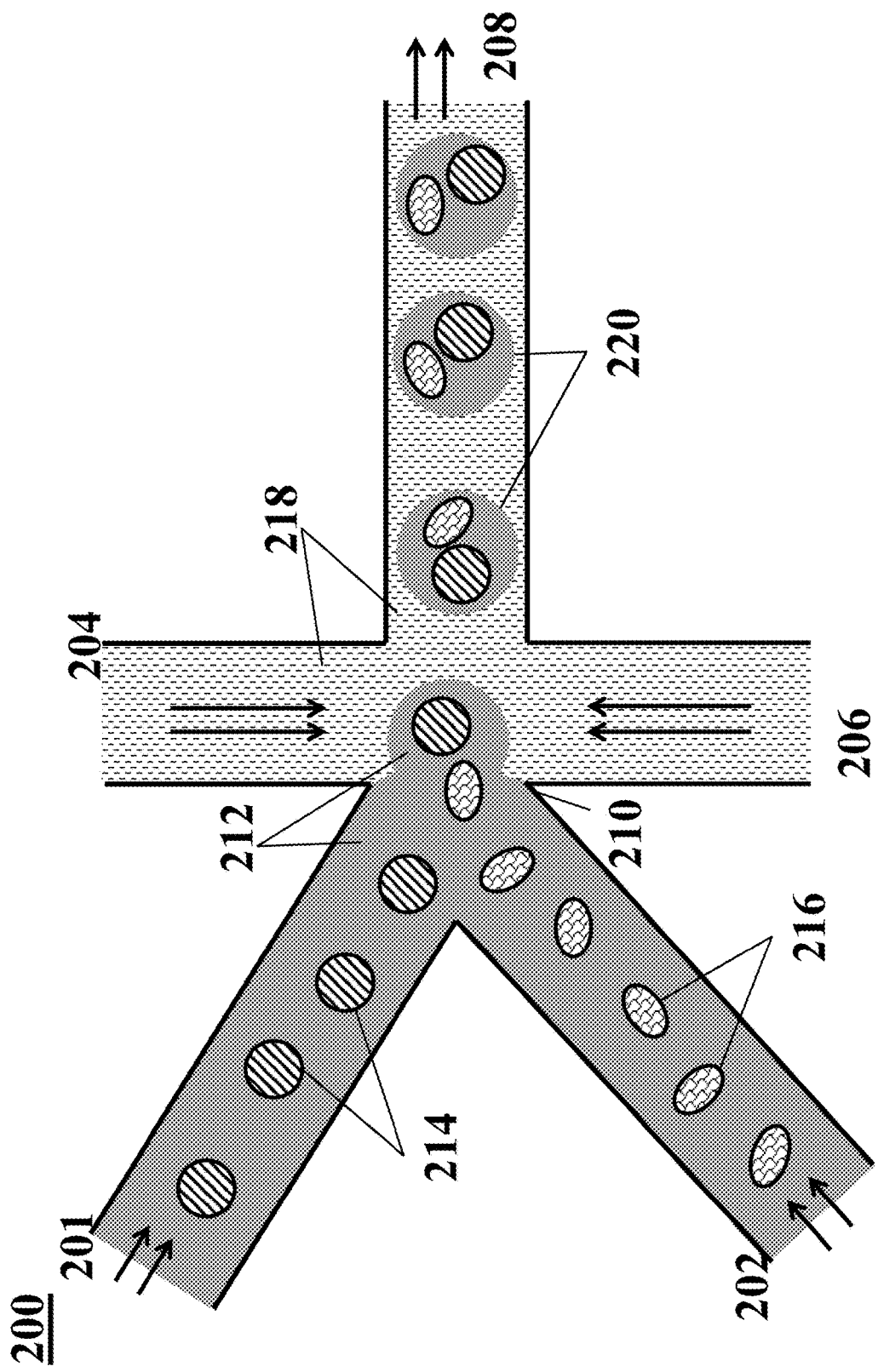
FIG. 2 shows an example of a microfluidic channel structure for delivering barcode carrying beads to droplets.

As will be appreciated, the above-described occupancy rates are also applicable to partitions that include both biological particles (or analyte carriers) and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles (or analyte carriers) may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of microcapsules comprising biological particles (or analyte carriers) may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles (or analyte carriers) can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle (or analyte carrier) can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle (or analyte carrier, such as a cell) may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. A cell bead may include a single nucleus. A cell bead may include a single, permeabilized nucleus. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents). A cell bead may comprise nucleic acid molecules comprising one or more functional sequences (e.g., 908, 909, and/or 910).

Encapsulated biological particles (or analyte carriers) can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned analyte carrier. For example, barcodes may be injected into droplets previous to, subsequent to, or concurrently with droplet generation. The delivery of the barcodes to a particular partition allows for the later attribution of the characteristics of the individual analyte carrier to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 (or analyte carriers) along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle (or analyte carrier) and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 m, 250 μm, 500 m, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligo-nucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or poly-nucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequenc-ing. Examples of such nucleic acid molecules (e.g., oligo-nucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
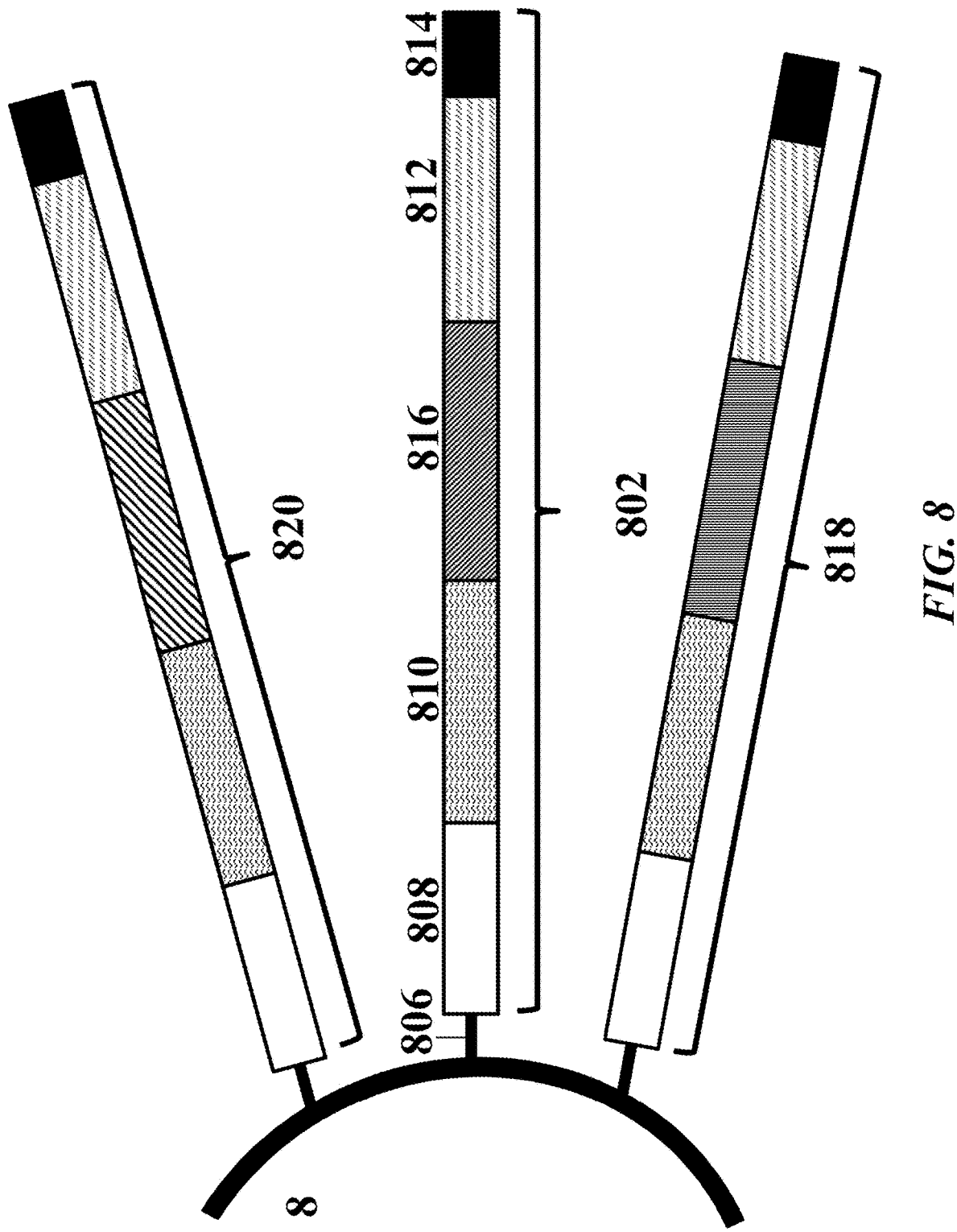
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular iden-tifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid mol-ecules can comprise both common sequence segments or relatively common sequence segments (e.g., 808, 810, 812, etc.) and variable or unique sequence segments (e.g., 816) between different individual nucleic acid molecules coupled to the same bead.

In operation, an analyte carrier (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the analyte carrier (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, an analyte carrier (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead.

Figure 22:
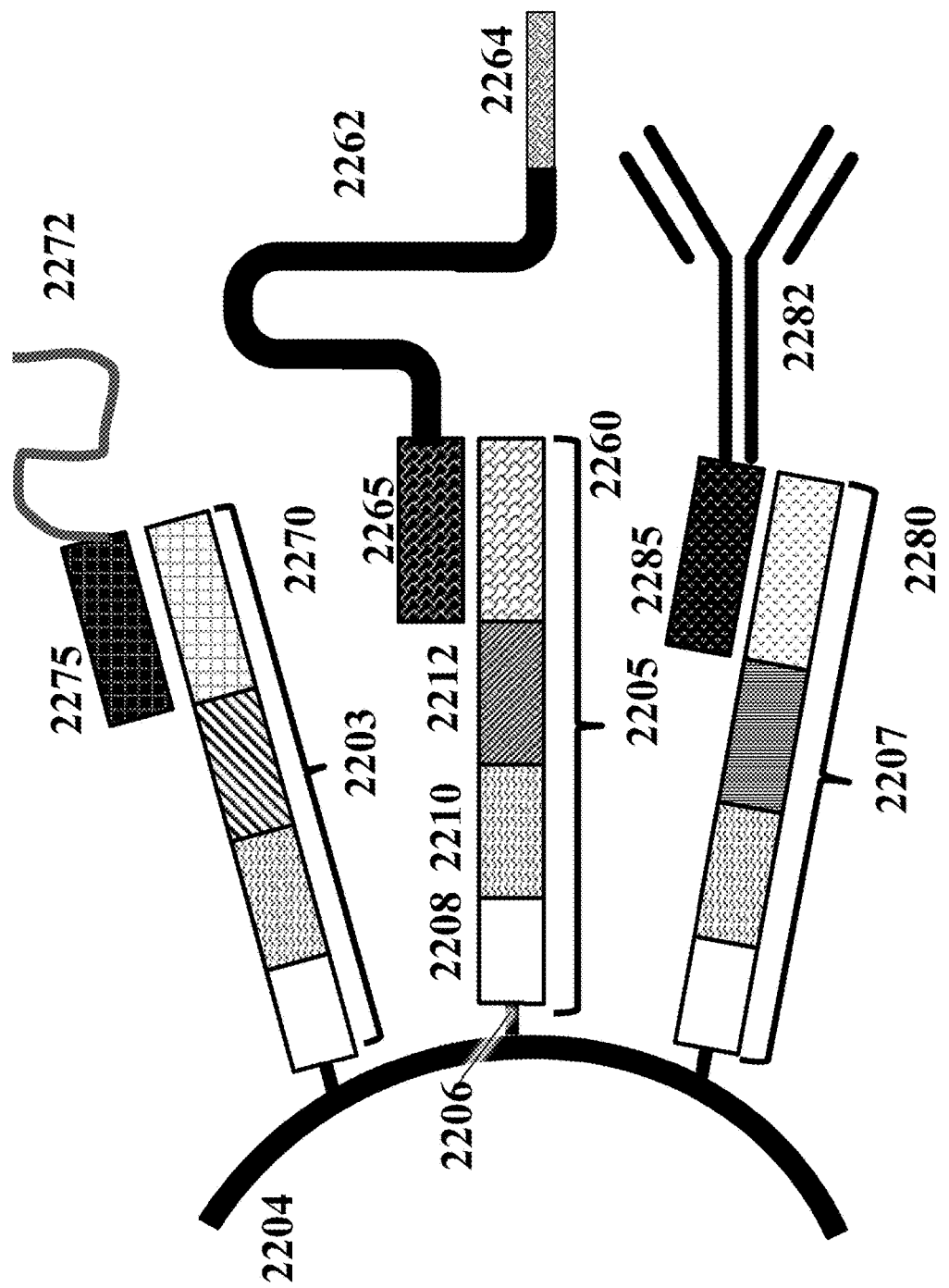
FIG. 22 illustrates another example of a barcode carrying bead.

FIG. 22 illustrates another example of a barcode carrying bead. A nucleic acid molecule 2205, such as an oligonucleotide, can be coupled to a bead 2204 by a releasable linkage 2206, such as, for example, a disulfide linker. The nucleic acid molecule 2205 may comprise a first capture sequence 2260. The same bead 2204 may be coupled (e.g., via releasable linkage) to one or more other nucleic acid molecules 2203, 2207 comprising other capture sequences. The nucleic acid molecule 2205 may be or comprise a barcode. As noted elsewhere herein, the structure of the barcode may comprise a number of sequence elements, such as a functional sequence 2208 (e.g., flow cell attachment sequence, sequencing primer sequence, etc.), a barcode sequence 2210 (e.g., bead-specific sequence common to bead, partition-specific sequence common to partition, etc.), and a unique molecular identifier 2212 (e.g., unique sequence within different molecules attached to the bead). The capture sequence 2260 may be configured to attach to a corresponding capture sequence 2265. In some instances, the corresponding capture sequence 2265 may be coupled to another molecule that may be an analyte or an intermediary carrier. For example, as illustrated in FIG. 22, the corresponding capture sequence 2265 is coupled to a guide RNA molecule 2262 comprising a target sequence 2264, wherein the target sequence 2264 is configured to attach to the analyte. Another oligonucleotide molecule 2207 attached to the bead 2204 comprises a second capture sequence 2280 which is configured to attach to a second corresponding capture sequence 2285. As illustrated in FIG. 22, the second corresponding capture sequence 2285 is coupled to an antibody 2282. In some cases, the antibody 2282 may have binding specificity to an analyte (e.g., surface protein). Alternatively, the antibody 2282 may not have binding specificity. Another oligonucleotide molecule 2203 attached to the bead 2204 comprises a third capture sequence 2270 which is configured to attach to a second corresponding capture sequence 2275. As illustrated in FIG. 22, the third corresponding capture sequence 2275 is coupled to a molecule 2272. The molecule 2272 may or may not be configured to target an analyte. The other oligonucleotide molecules 2203, 2207 may comprise the other sequences (e.g., functional sequence, barcode sequence, UMI, etc.) described with respect to oligonucleotide molecule 2205. While a single oligonucleotide molecule comprising each capture sequence is illustrated in FIG. 22, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 2204 may comprise other capture sequences. Alternatively or in addition, the bead 2204 may comprise fewer types of capture sequences (e.g., two capture sequences). Alternatively or in addition, the bead 2204 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic cofactors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about $\frac{1}{10}$th, less than about $\frac{1}{50}$th, or even less than about $\frac{1}{100}$th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle (or analyte carrier) and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned analyte carriers and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, analyte carriers may be partitioned along with lysis reagents in order to release the contents of the analyte carriers within the partition. In such cases, the lysis agents can be contacted with the analyte carrier suspension concurrently with, or immediately prior to, the introduction of the analyte carriers into the partitioning junction/droplet generation zone (e.g., junction 210), such as through an additional channel or channels upstream of the channel junction. In accordance with other aspects, additionally or alternatively, analyte carriers may be partitioned along with other reagents, as will be described further below.

Figure 3:
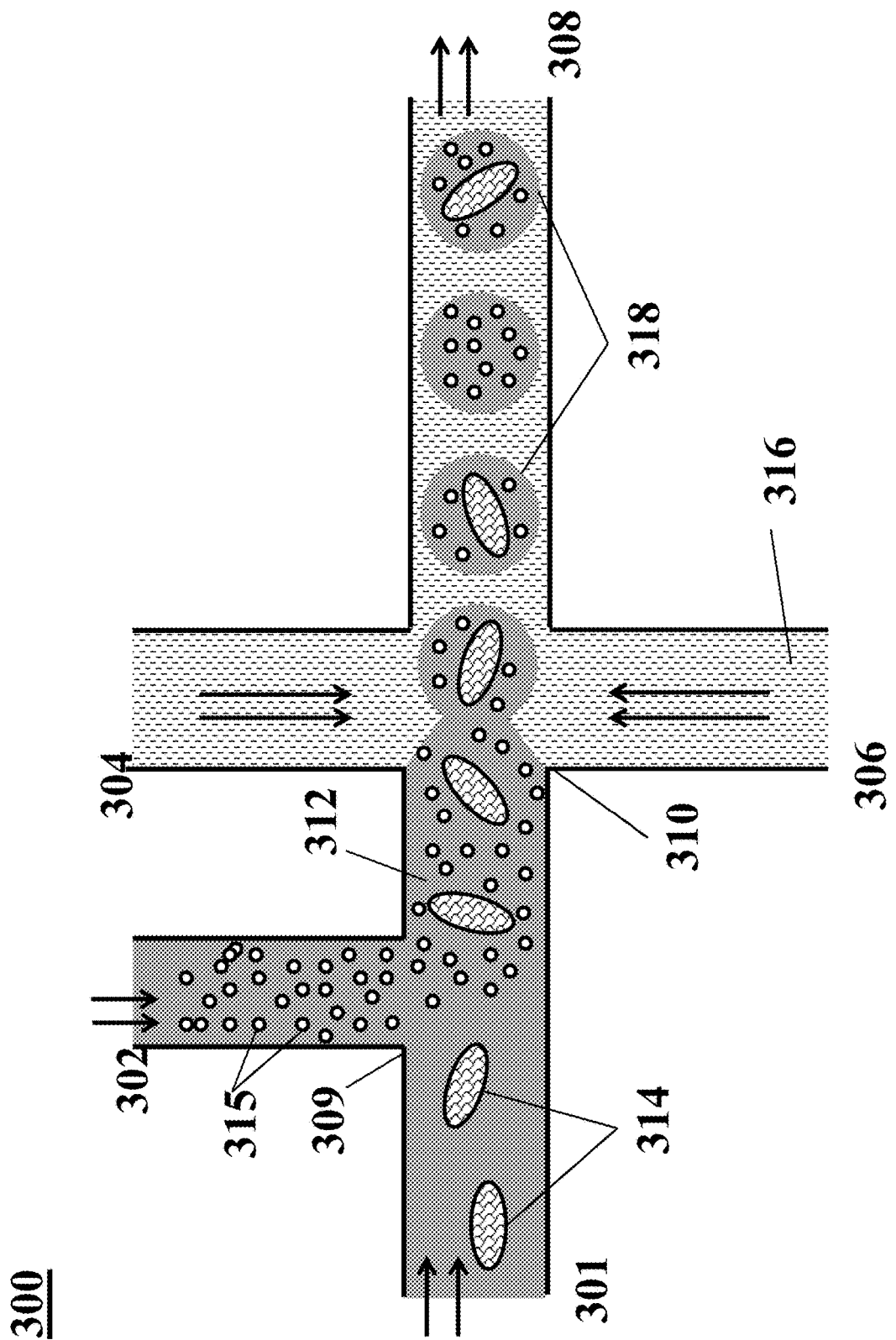
FIG. 3 shows an example of a microfluidic channel structure for co-partitioning biological particles and reagents.

FIG. 3 shows an example of a microfluidic channel structure 300 for co-partitioning biological particles (or analyte carriers) and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 (or analyte carriers) along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles (or analyte carriers) are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or analyte carriers that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the analyte carriers to cause the release of the analyte carriers's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of analyte carriers that may be in addition to or in place of droplet partitioning, where any pore size of the encapsulate is sufficiently small to retain nucleic acid fragments of a given size, following cellular disruption.

Alternatively or in addition to the lysis agents co-partitioned with the analyte carriers described above, other reagents can also be co-partitioned with the analyte carriers, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated analyte carriers, the analyte carriers may be exposed to an appropriate stimulus to release the analyte carriers or their contents from a co-partitioned microcapsule. For example, in some cases, a chemical stimulus may be co-partitioned along with an encapsulated analyte carrier to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated analyte carrier to be released into a partition at a different time from the release of nucleic acid molecules into the same partition.

Additional reagents may also be co-partitioned with the analyte carriers, such as endonucleases to fragment an analyte carrier's DNA, DNA polymerase enzymes and dNTPs used to amplify the analyte carrier's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of analyte carriers, such as RNA, DNA, or proteins) contained therein may be further processed within the partitions. In accordance with the methods and systems described herein, the macromolecular component contents of individual analyte carriers can be provided with unique identifiers such that, upon characterization of those macromolecular components they may be attributed as having been derived from the same analyte carrier or particles. The ability to attribute characteristics to individual analyte carriers or groups of analyte carriers is provided by the assignment of unique identifiers specifically to an individual analyte carrier or groups of analyte carriers. Unique identifiers, e.g., in the form of nucleic acid barcodes can be assigned or associated with individual analyte carriers or populations of analyte carriers, in order to tag or label the analyte carrier's macromolecular components (and as a result, its characteristics) with the unique identifiers. These unique identifiers can then be used to attribute the analyte carrier's components and characteristics to an individual analyte carrier or group of analyte carriers.

In some aspects, this is performed by co-partitioning the individual analyte carrier or groups of analyte carriers with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual analyte carrier, or to other components of the analyte carrier, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned analyte carriers. These sequences include, e.g., targeted or random/universal amplification primer sequences for amplifying the genomic DNA from the individual analyte carriers within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of analyte carriers, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
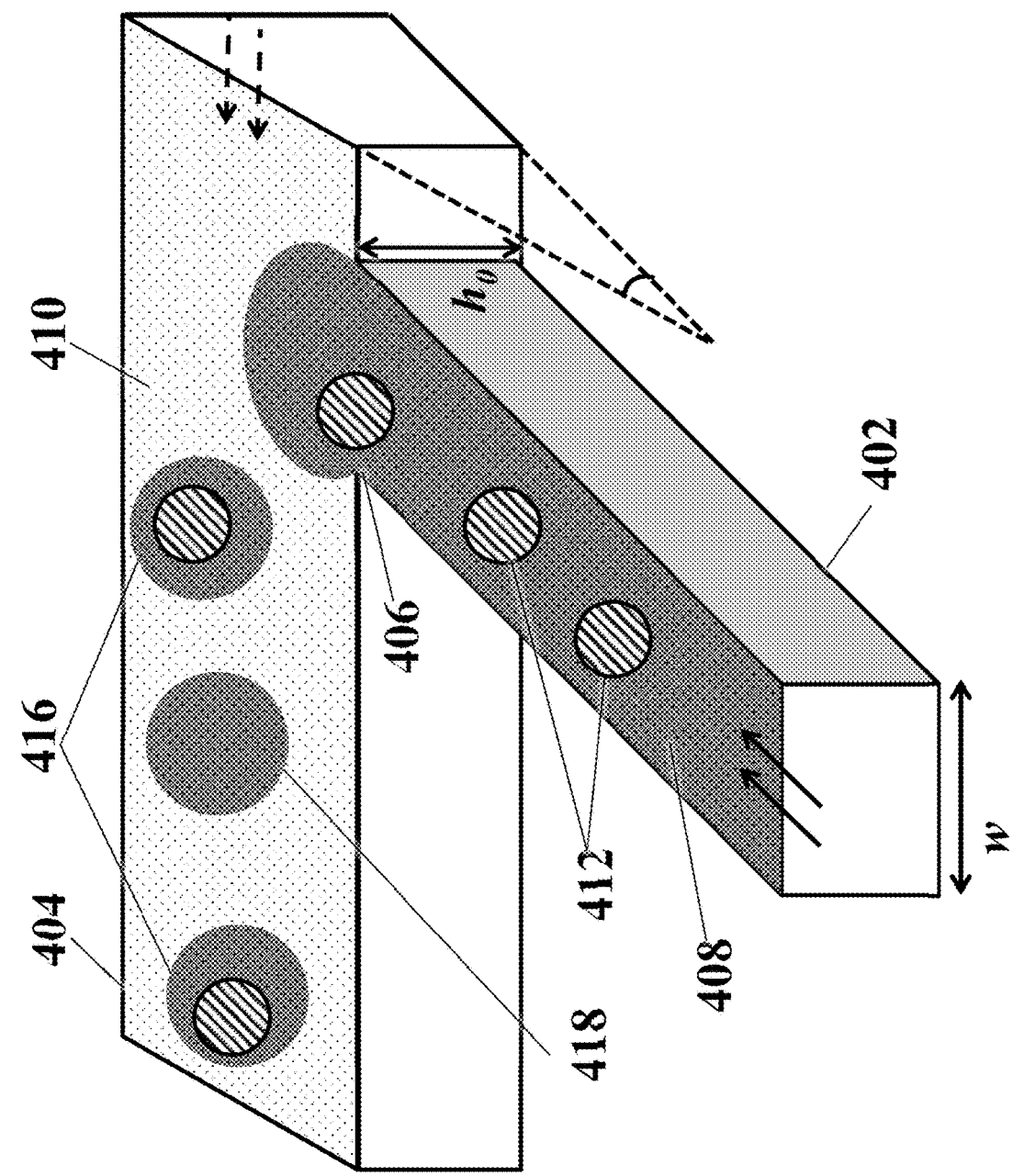
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more analyte carriers, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (or analyte carriers, e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, α. The expansion angle, α, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, a, may be between a range of from about 0.5° to about 4°, from about 0.1° to about 10°, or from about 00 to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 90°, 8°, 7°, 6°, 5°, 4°, 30°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 L/min, 50 μL/min, 55 μL/min, 60 μL/min, 65 μL/min, 70 μL/min, 75 μL/min, 80 μL/min, 85 μL/min, 90 μL/min, 95 L/min, 100 μL/min, 110 L/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
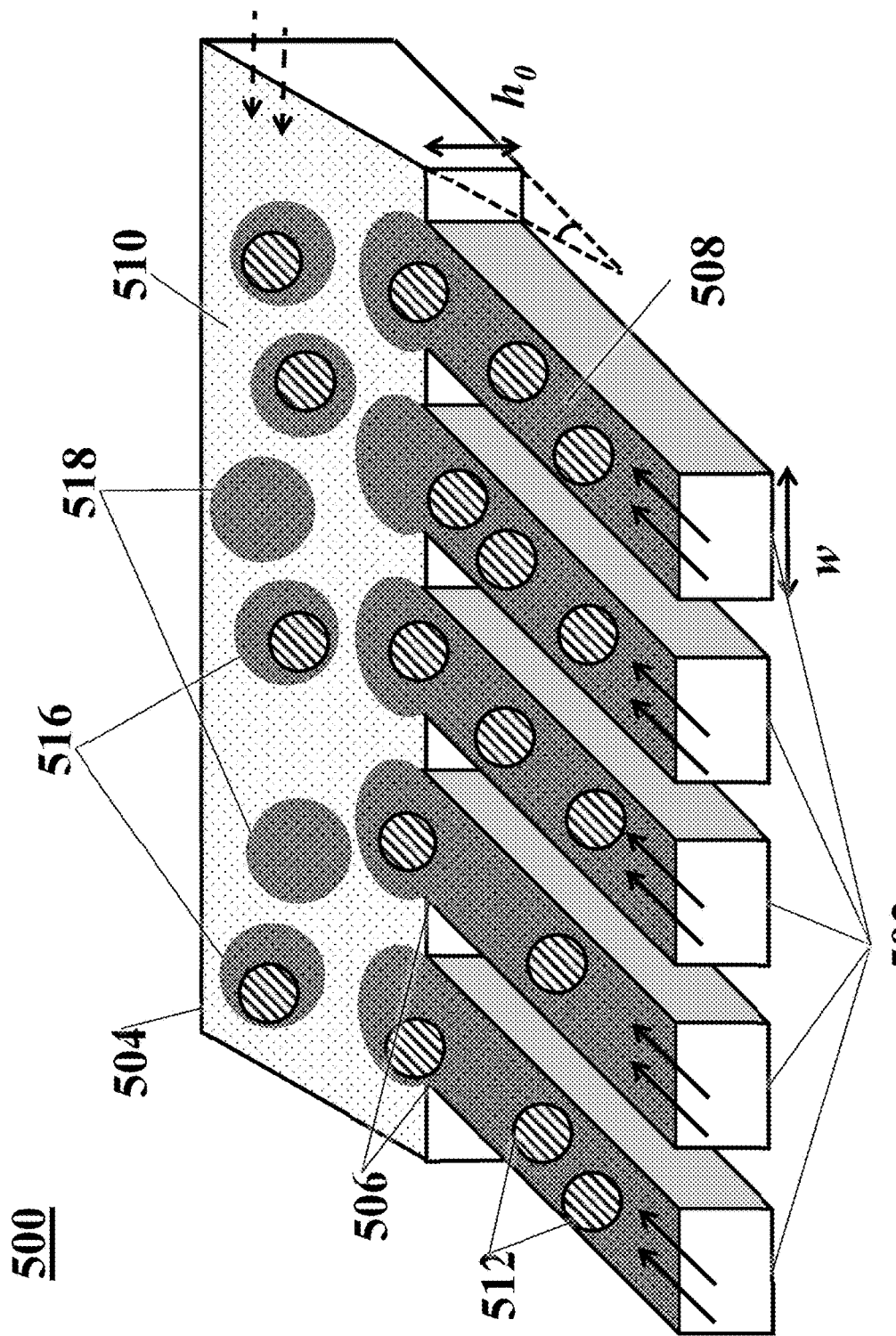
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
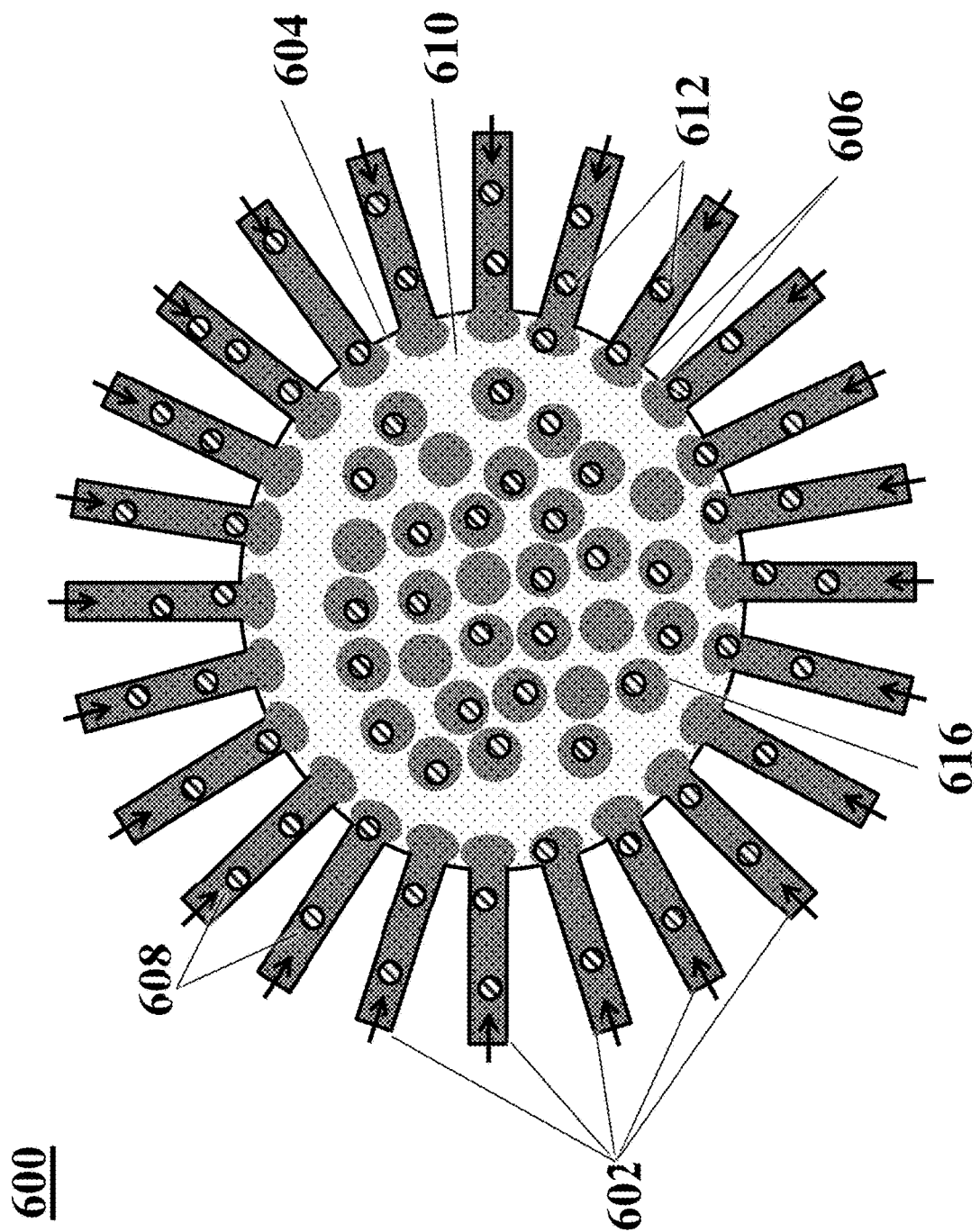
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, a (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or analyte carrier injected into the droplets may or may not have uniform size.

Figure 7A:
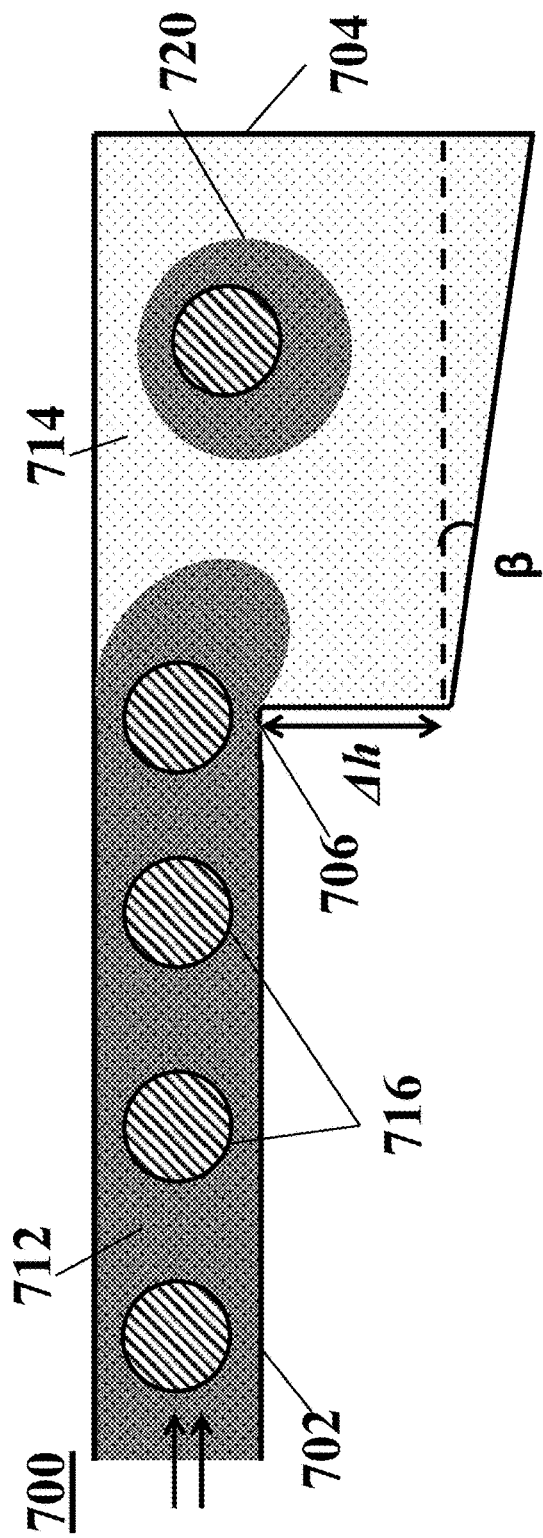
FIG. 7A shows a cross-section view of another example of a microfluidic channel structure with a geometric feature for controlled partitioning.
Figure 7B:
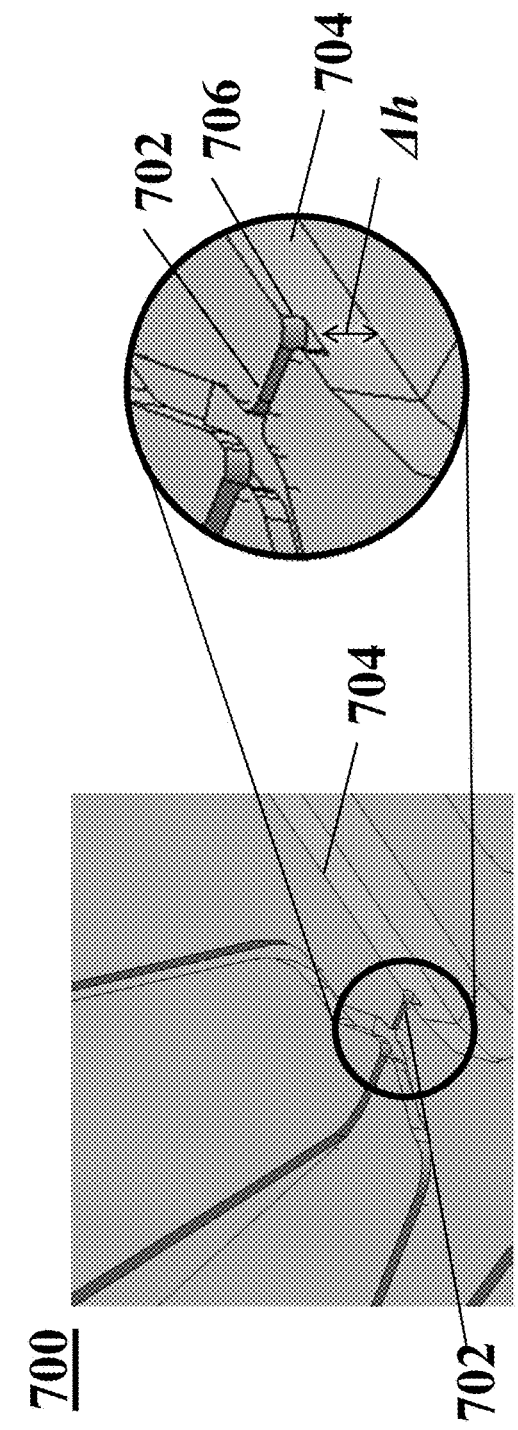
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, analyte carrier, macromolecular constituents of analyte carrier, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of Δh. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, β, at or near the junction 706. The height difference, Δh, and/or expansion angle, β, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different analyte carrier or organism types within a population of analyte carriers, including, for example, microbiome analysis and characterization, environmental testing, food safety testing, epidemiological analysis, e.g., in tracing contamination or the like.

Computer Systems

Figure 21:
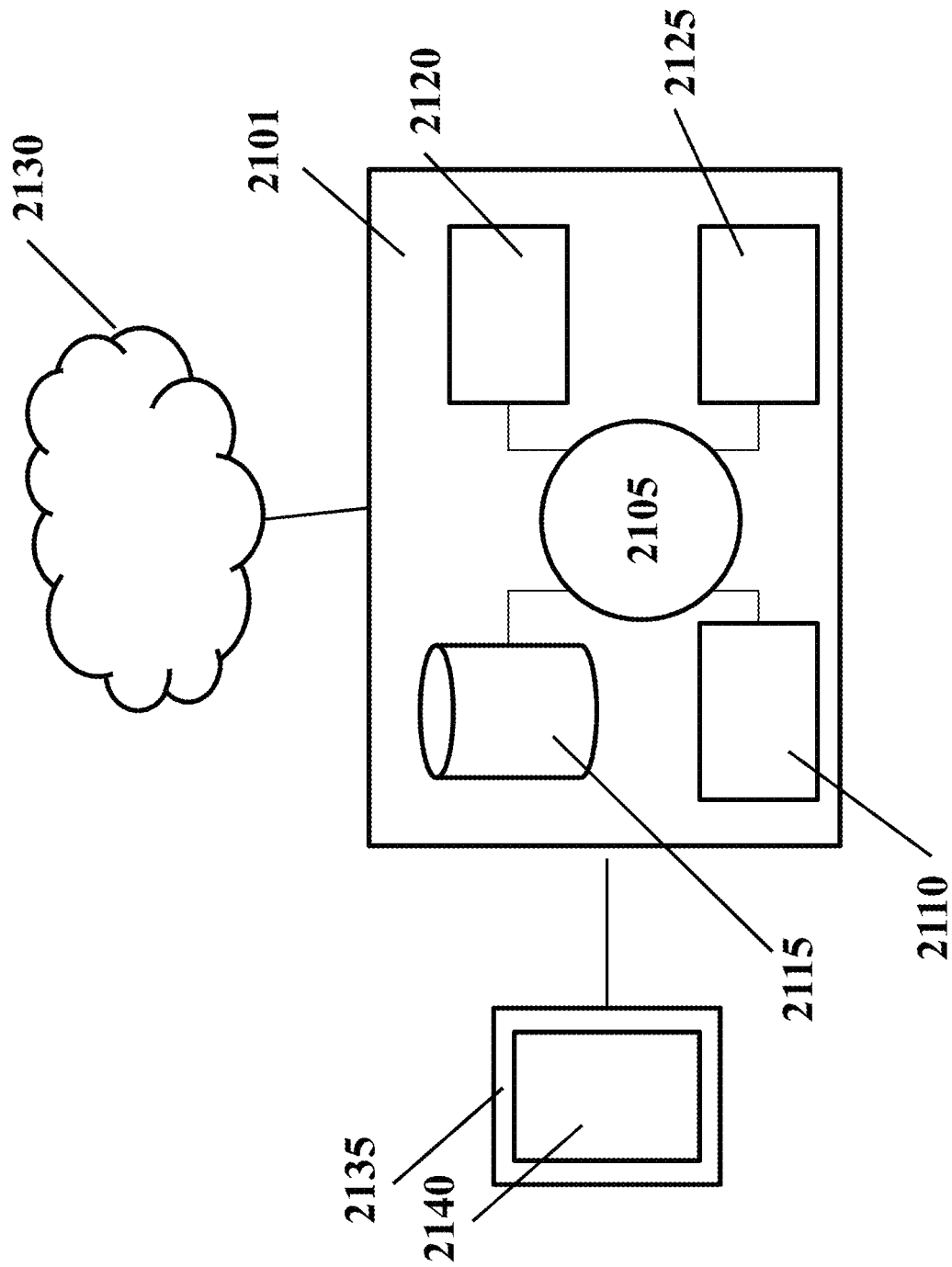
FIG. 21 shows a computer system that is programmed or otherwise configured to implement methods provided herein.

The present disclosure provides computer systems that are programmed to implement methods of the disclosure. FIG. 21 shows a computer system 2101 that is programmed or otherwise configured to (i) control a microfluidics system (e.g., fluid flow), (ii) sort occupied droplets from unoccupied droplets, (iii) polymerize droplets, (iv) perform sequencing applications, (v) generate and maintain a library of barcode beads, and (vi) analyze nucleic acid sequences. The computer system 2101 can regulate various aspects of the present disclosure, such as, for example, regulating fluid flow rate in one or more channels in a microfluidic structure and regulating polymerization application units. The computer system 2101 can be an electronic device of a user or a computer system that is remotely located with respect to the electronic device. The electronic device can be a mobile electronic device.

The computer system 2101 includes a central processing unit (CPU, also "processor" and "computer processor" herein) 2105, which can be a single core or multi core processor, or a plurality of processors for parallel processing. The computer system 2101 also includes memory or memory location 2110 (e.g., random-access memory, read-only memory, flash memory), electronic storage unit 2115 (e.g., hard disk), communication interface 2120 (e.g., network adapter) for communicating with one or more other systems, and peripheral devices 2125, such as cache, other memory, data storage and/or electronic display adapters. The memory 2110, storage unit 2115, interface 2120 and peripheral devices 2125 are in communication with the CPU 2105 through a communication bus (solid lines), such as a motherboard. The storage unit 2115 can be a data storage unit (or data repository) for storing data. The computer system 2101 can be operatively coupled to a computer network ("network") 2130 with the aid of the communication interface 2120. The network 2130 can be the Internet, an internet and/or extranet, or an intranet and/or extranet that is in communication with the Internet. The network 2130 in some cases is a telecommunication and/or data network. The network 2130 can include one or more computer servers, which can enable distributed computing, such as cloud computing. The network 2130, in some cases with the aid of the computer system 2101, can implement a peer-to-peer network, which may enable devices coupled to the computer system 2101 to behave as a client or a server.

The CPU 2105 can execute a sequence of machine-readable instructions, which can be embodied in a program or software. The instructions may be stored in a memory location, such as the memory 2110. The instructions can be directed to the CPU 2105, which can subsequently program or otherwise configure the CPU 2105 to implement methods of the present disclosure. Examples of operations performed by the CPU 2105 can include fetch, decode, execute, and writeback.

The CPU 2105 can be part of a circuit, such as an integrated circuit. One or more other components of the system 2101 can be included in the circuit. In some cases, the circuit is an application specific integrated circuit (ASIC).

The storage unit 2115 can store files, such as drivers, libraries and saved programs. The storage unit 2115 can store user data, e.g., user preferences and user programs. The computer system 2101 in some cases can include one or more additional data storage units that are external to the computer system 2101, such as located on a remote server that is in communication with the computer system 2101 through an intranet or the Internet.

The computer system 2101 can communicate with one or more remote computer systems through the network 2130. For instance, the computer system 2101 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2101 via the network 2130.

Methods as described herein can be implemented by way of machine (e.g., computer processor) executable code stored on an electronic storage location of the computer system 2101, such as, for example, on the memory 2110 or electronic storage unit 2115. The machine executable or machine readable code can be provided in the form of software. During use, the code can be executed by the processor 2105. In some cases, the code can be retrieved from the storage unit 2115 and stored on the memory 2110 for ready access by the processor 2105. In some situations, the electronic storage unit 2115 can be precluded, and machine-executable instructions are stored on memory 2110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2101 can include or be in communication with an electronic display 2135 that comprises a user interface (UI) 2140 for providing, for example, results of sequencing analysis. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 2105. The algorithm can, for example, perform sequencing and analyze sequencing results.

EXAMPLES

Example 1: Single Cell Epigenetic Profiling

Cells are isolated from a subject. The nuclei from the cells are isolated, permeabilized, and partitioned into droplets comprising polymeric precursors, such that each droplet comprises at most one nucleus. The droplets also comprise magnetic particles. The polymeric precursors are subjected to conditions sufficient to polymerize the precursors, such that cell beads are generated each comprising a single permeabilized nucleus and at least one magnetic particle. Cell beads are placed in an aqueous solution comprising an antibody and an engineered MNase covalently linked to Protein A. The engineered MNase comprises a biotin molecule on its surface near the active site of the enzyme. The antibody is capable of binding Histone H2A protein. The antibody molecules are allowed to bind to the Histone H2A proteins in the nuclei of the cell beads, and the engineered MNase attached to Protein A is allowed to bind to the antibody molecules. Unbound antibody and engineered MNase is removed by washing.

The cell beads comprising the antibody and engineered MNase bound to the Histone H2A proteins are partitioned into a droplet together with a barcode bead in an aqueous solution comprising $Mg^{2+}$, $Ca^{2+}$, a ligase enzyme, and a functionalized dextran polymer. The barcode bead comprises Y-adapter nucleic acid barcode molecules attached thereto. The functionalized dextran polymer is attached to streptavidin molecules. The $Mg^{2+}$ and $Ca^{2+}$ diffuse into the cell bead, thereby activating the engineered MNase. The engineered MNase cleaves the genomic DNA in the chromatin of the nucleus near Histone H2A proteins, thereby generating DNA fragments. The DNA fragments and the engineered MNase diffuse out of the cell bead into the droplet. The biotin molecule on the engineered MNase binds to the streptavidin molecule on the functionalized dextran polymer, thereby inactivating the engineered MNase.

The Y-adapter nucleic acid barcode molecules are released from the barcode bead into the droplet. The ligase enzyme ligates the Y-adapter nucleic acid barcode molecules onto the DNA fragments, generating barcoded DNA fragments. The barcoded DNA fragments and cell bead are released from the droplet into a solution, and the cell bead is removed from the solution by magnetic purification. The barcoded DNA fragments are purified and subjected to nucleic acid sequencing to generate nucleic acid sequences from a single cell. Analysis of these nucleic acid sequences is performed to generate an epigenetic profile of the single cell.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a analyte carrier (e.g., a cell or cell bead) is partitioned in a partition (e.g., droplet), and multiple analytes from the analyte carrier are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:
1. A method comprising:
   (a) providing a cell bead comprising (i) a nucleus and (ii) a nuclease coupled to a ligand;
   (b) using said nuclease to cleave chromatin in said nucleus, thereby generating a cleaved nucleic acid molecule;
   (c) partitioning (i) said cell bead, (ii) a plurality of nucleic acid barcode molecules, and (iii) a functionalized polymer to generate a partition, wherein said functionalized polymer is selected from the group consisting of dextran, polyethylene glycol (PEG), and polyacrylamide;

(d) outside of said cell bead in said partition, using said functionalized polymer to bind to said nuclease via said ligand; and (e) using said cleaved nucleic acid molecule or a derivative thereof and a nucleic acid barcode molecule of said plurality of nucleic acid barcode molecules to perform one or more reactions in said partition to generate a barcoded nucleic acid molecule.

2. The method of claim 1, wherein said partition is a droplet or a well.

3. The method of claim 1, wherein said one or more reactions are performed outside said cell bead.

4. The method of claim 1, wherein said one or more reactions comprise nucleic acid extension, nucleic acid amplification, or nucleic acid ligation.

5. The method of claim 1, wherein said cell bead is functionalized.

6. The method of claim 1, wherein said functionalized polymer is positively charged or negatively charged.

7. The method of claim 1, wherein said partition comprises a cation for activating said nuclease.

8. The method of claim 7, wherein said cation is magnesium or calcium.

9. The method of claim 1, wherein said nuclease is micrococcal nuclease (MNase) or a deoxyribonuclease (DNase).

10. The method of 1, wherein said nuclease is an engineered nuclease.

11. The method of claim 10, further comprising binding said ligand of said engineered nuclease to a binding partner coupled to said functionalized polymer, wherein said binding partner inhibits activity of said engineered nuclease.

12. The method of claim 1, wherein said nucleic acid barcode molecule is attached to a bead.

13. The method of claim 1, wherein said nucleic acid barcode molecule is attached to a bead, wherein said bead is a gel bead.

14. The method of claim 1, wherein said functionalized polymer comprises a linear polymer or a branched polymer.

15. The method of claim 1, wherein said functionalized polymer is not cross-linked.

16. The method of claim 1, wherein said partition further comprises a magnetic particle.

17. The method of claim 16, wherein said magnetic particle comprises, attached thereto, a nucleic acid molecule comprising a capture sequence.

18. The method of claim 17, wherein said capture sequence is a poly-T sequence, a random N-mer sequence, or a targeted capture sequence.

19. The method of claim 1, wherein said functionalized polymer is incapable of diffusing into said cell bead.

\* \* \* \* \*